United States Patent [19]

Kitano et al.

[11] Patent Number: 5,543,322
[45] Date of Patent: Aug. 6, 1996

[54] DNA CODING FOR ALKALINE PROTEASE

[75] Inventors: Kazuaki Kitano, Sakai; Shigeru Morita, Higashiosaka; Masato Kuriyama, Osaka; Kazutaka Maejima, Kawanishi, all of Japan

[73] Assignee: Takeda Chemical Industries, Ltd., Osaka, Japan

[21] Appl. No.: 289,653

[22] Filed: Aug. 12, 1994

Related U.S. Application Data

[63] Continuation of Ser. No. 887,284, May 22, 1992, abandoned.

[30] Foreign Application Priority Data

May 21, 1991 [JP] Japan ................................. 3-117360

[51] Int. Cl.$^6$ .................... C12N 15/31; C12N 15/63; C12N 15/74; C12N 15/70
[52] U.S. Cl. .................... 435/252.3; 435/252.33; 435/320.1; 536/24.1
[58] Field of Search .................... 435/320.1, 252.3, 435/252.33, 256.5, 256.1, 69.8; 536/24.1

[56] References Cited

U.S. PATENT DOCUMENTS 3,655,570  4/1972  Isono et al. ............................ 252/132

FOREIGN PATENT DOCUMENTS 0133756  3/1985  European Pat. Off. .
88007581  10/1988  WIPO .

OTHER PUBLICATIONS

Journal of The Takeda Research Laboratories vol. 38, No. 1–2, 1979, JP pp. 33–43, K. Tomodo et al. "Production, purification and general properties of Fusarium alkaline protease."Biochemical and Biophysical Research Communications vol. 145, No. 2, Jun. 15, 1987, New York pp. 712–718, K. Yoshimura et al. "Differences between *Saccharomyces cerevisiae* and *Bacillus subtilis* in secrection of human lysozyme."Database WPIL Week 8841, Derwent Publications Ltd., London, GB; An 88–290577 (41) & JP–A–63 214 187 (Mitsubishi Gas Chem KK) Sep. 6, 1988 *abstract*.

Journal of the Takeda Research Laboratories vol. 38 "Production, Purification and General Properties of Fusarium Alkaline Protease" (1979) Tomoda et al. pp. 33–43.

Agriculture and Biological Chemistry vol. 38 "Screening of Fungi Producing Alkaline Protease From n–Paraffins and Iduction of Kabicidin Resistant Mutant of Fusarium sp" (1974) Suzuki et al. pp. 135–139.

Biotechnology, Dec. 1988, vol. 6 No. 12, "High Level Expression of Recombinant Genes in Aspergillus Oryzae" Christensen et al. pp. 1419–1422.

Database WPIL Week 9040, Derwent Publications Ltd., London, GB; An 90–301017 (40) & JP–A–2 211 869 Shokuhin Sangyo Kos) 23 Aug. 1990 *abstract*.

Tomoda et al (1979) J. Takeda Res Lab 38:33–43.

Tatsumi (1989) Mol Gen Genet 219:33–38.

Igogai (Feb. 1991) Agric Biol Chem 55:471–477.

Lee (1988) Science 239:1288–1291.

*Primary Examiner*—Charles L. Patterson, Jr.
*Attorney, Agent, or Firm*—Wenderoth, Lind & Ponack

[57] ABSTRACT

There are disclosed cloning of an alkaliprotease secretion gene of a mold and a DNA fragment containing a part or all of the alkaliprotease gene. A plasmid into which the DNA fragment is integrated, a transformant obtained by using the plasmid and the production of a useful protein by using the transformant are also disclosed.

9 Claims, 19 Drawing Sheets

FIG. 1a

```
1                                                  50
ggatccgaaagatgagaccgctttcatgctcacacttgctagtccaccga 51                                                 100
cggcatatggccaagatgccactccacgccattattccgggagtttcgct 101                                                150
tctcgactcgcagaacccactcctccaatatcatcaaactagcattgatc 151                                                200
gagaagctccaaaggcacagtgtcgcattgtacagagggattggcaattc 201                                                250
gccgctgtcccatggcctcaagaccttccagattctctcagctcagctca 251                                                300
tctgacaaattaagctcagcagcatcgcctcttctttattgatcctttgt 301                                                350
tctagcccaagtcccccgtcgcatccacgctggaaatggcaggtagcaag 351                                                400
aacttgttcgacattgaagagtgggatgccgactcgccgaagattgagta 401                                                450
gctcgtccagcaaagacgacggtgaaagataaatagcagctgcggcccg 451                                                500
tgaaatgaattgttcctcatcaagctcacagtttcattagcaaacagtct 501                                                550
tccaaaaactcacttctcaaccttcatactccctgacaagATGCGTCTG 551                                                600
TCCATCATCGCAGTCCTTCCCCTGGCCCTCGCGGCCCCGGTCCTGGAACC 601                                                650
CGCTCCTCTCCTCGAGGCTCGTGGTTCGCAGCCCATTGCTGGCAAGTACA 651                                                700
TTGTCAAGCTCAAGGACACCGCCAAGATTGGCATCATGGAGGCCACGGCC 701                                                750
AAGGTGGCCAACCCTGAACGTGTCTACCAGAACGTCATCAAGGGATTCTC 751                                                800
CGCTTCCCTCAGCAAGGAAGAGGTTGAGCGTCTCCGCCACGACCCTGATg 801                                                850
taagtgcaacacgttgtactaaagtaagacgacgttgaccattttggga
```

FIG. 1b

```
851                                              900
aatagGTCGAGTCTATTGAGCAGGATGCCATCATCAGCATCAACGCTATT 901                                              950
ACCCAGCAGCAGGGCGCAACTTGGGGACTTACCCGCATCTCCCACCGCCA 951                                             1000
GCGTGGCAGCACCGCGTATGCCTACGACACGACCGCCGGACAGGGTGCCT 1001                                            1050
GCGCCTATGTCATTGACACCGGTGTTGAGGACACTCACCCCgtaagctct 1051                                            1100
tgcatgtttatggtcaaaatgtatgccagttgctaatggaagtgaaatgt 1101                                            1150
agGAGTTTGAAGGACGTGCCAAGCAGATCAAGACCTTTGCCAGCACCGCC 1151                                            1200
CGTGACGGCAACGGCCACGGCACCCACTGCTCCGGCACCATTGGCTCCAA 1201                                            1250
AACATATGGTGTCGCCAAGAAGGTCTCCATCTTCGGTGTCAAGGTCCTGG 1251                                            1300
ACGACAACGGCTCGGGCTCGCTCAGCAATGTCATTGCCGGCATGGACTTT 1301                                            1350
GTCGCCTCTGACTACCGCTCTCGCAACTGCCCTCGTGGTGTCGTTGCCAG 1351                                            1400
CATGTCTCTTGGTGGTGGTTACTCGGCCACCGTGAACCAGGCTGCCGCCC 1401                                            1450
GTCTGCAGTCCTCTGGCGTCTTTGTCGCTGTCGCCGCTGGCAACGACAAC 1451                                            1500
CGTGATGCTGCCAACACTTCGCCCGCCTCGGAGCCCTCGGTTTGCACCGT 1501                                            1550
CGGCGCTACTGACTCGTCCGATCGTCGCTCGTCTTTCTCCAACTATGGTC 1551                                            1600
GTGCCCTTGATATTTTCGCTCCCGGCACTGACATCACCTCCACCTGGATT 1601                                            1650
GGCGGCCGCACGgtaagttcctgtcgcgttttgtggtcttgtgttccaga 1651                                            1700
caactaacctgttgactctagAACACCATCTCTGGAACCTCCATGGCTAC
```

FIG. 1c

```
1701                                                      1750
TCCCCACATTGCTGGTCTCGGTGCCTACCTTCTGGCTCTCGAGGGTGGCA 1751                                                      1800
GTGCCAGCACTATCTGTGCTCGTATCCAGACTCTCTCCACCAAGAATGCC 1801                                                      1850
ATCTCGGGCGTTCCCTCGGGTACCGTCAACTACCTGGCCTTCAACAACGC 1851                                                      1900
CACGTGAgtgagtcagtaatcactcatctggaggcatgaaggctggatga 1901                                                      1950
acggagggcgcatgtcctatacaactgccggtcagcaatgttaatgcaga 1951                                                      2000
cctcatcgctgcctagggatcgattgccgaggtattggtttcatttgct 2001                                                      2050
ttttatgtgactttgaggtgtctcctccgccaagtacatagtcaataaga 2051                                                      2100
gtgttttgcactatacgaacagccaccgtgacccgtaaagcatcgcagcc 2101                                                      2150
atggcgttctcttgtgacgcatctgtatgtatgcttctggagatttacag 2151                                                      2200
agaaaattaactctattcggacaatttacgaaggatgcagtaccctgcac 2201                                                      2250
gagccgacagctcggcacatcgagaatcttcagctgggagagctgaagcc 2251                                                      2300
tcgataccaaagtcacatgctatactttggtggcttgattatatcagaat 2301                                                      2350
tgcgacatcggtacagattgatcatttaaggcaaccatcagtttatttc 2351                                                      2400
cagccacgtcaacatggcgttatggctggttttgggcgtgaatcggtaac 2401                                                      2450
tgcacccgacgaagcaggtggagccgaccgtgggatggaaccggcttgtc 2451                                                      2500
agtttctcgccgtgggcacggaaaacacagccatccgggtacgcggacag 2501                                                      2550
gtcagagataattcaggcagccattgcacgagaatctgactagtccgtgc
```

FIG. 1d 2551                                                    2600
tggatttgtggttcaaaacagagcctgacaggcagccgagactagttgtt 2601                                                    2650
gacgtgcaggtcgcaaggggcacatggttatggtgtgctgtgaatgccga 2651                                                    2700
atgagttgaagggctcagtagtttgagtttgaacatggtgtccgttggc 2701                                                    2750
cgatgtggaggagagcaacaagtccacagttgcagctaacaagccagcca 2751                                                    2800
gccgcaagtgcaaagaaatgggtttaggacaatctcgtacaatggggatt 2801                                            2845
cgagtttcgttgctcctcgtttctttatttagaggtcctggatcc

FIG. 2a

```
1                                                           60
ATGCGTCTGTCCATCATCGCAGTCCTTCCCCTGGCCCTCGGCGCCGGGTCCTGGAACCC
MetArgLeuSerIleIleAlaValLeuProLeuAlaLeuAlaAlaProValLeuGluPro 61                                                          120
GCTCCTCCTCGAGGCTCGTGGTTCGCAGCCATTGCTGGCAAGTACATTGTCAAGCTC
AlaProLeuLeuGluAlaArgGlySerGlnProIleAlaGlyLysTyrIleValLysLeu 121                                                         180
AAGGACACCGCCAAGATTGGCATCATGGAGGCCACGGCCAAGGTGGCCAACCCTGAACGT
LysAspThrAlaLysIleGlyIleMetGluAlaThrAlaLysValAlaAsnProGluArg 181                                                         240
GTCTACCAGAACGTCATCAAGGATTCTCCGCTTCCCTCAGCAAGGAAGAGGTTGAGCGT
ValTyrGlnAsnValIleLysGlyPheSerAlaSerLeuSerLysGluGluValGluArg 241                                                         300
CTCCGCCACGACCCTGATGTCGAGTCTATTGAGCAGGATGCCATCATCAGCATCAACGCT
LeuArgHisAspProAspValGluSerIleGluGlnAspAlaIleIleSerIleAsnAla 301                                                         360
ATTACCCAGCAGCAGGGCGCAACTTGGGACTTACCCGCATCTCCACCGCCAGCGTGGC
IleThrGlnGlnGlnGlyAlaThrTrpGlyLeuThrArgIleSerHisArgGlnArgGly 361                                                         420
AGCACCGGGTATGCCTACGACACGACCCGGACACAGGGTGCCTGGCCTATGTCATTGAC
SerThrAlaTyrAlaTyrAspThrThrArgAlaGlyGlnGlyAlaCysAlaTyrValIleAsp 421                                                         480
ACCGGTGTTGAGGACACTCACCCCGAGTTTGAAGGACGTGCCAAGCAGATCAAGACCTTT
ThrGlyValGluAspThrHisProGluPheGluGlyArgAlaLysGlnIleIleLysThrPhe
```

FIG. 2b

```
481
GCCAGCACGGCCCGTGACGGCAACGGCACCGGCACCCACTGCTCCGGCACCATTGGCTCC    540
AlaSerThrAlaArgAspGlyAsnGlyThrGlyThrHisCysSerGlyThrIleGlySer

541
AAAACATATGGTGTCGCCAAGAAGGTCTCCATCTTCGGTGTCAAGGTCCTGGACGACAAC    600
LysThrTyrGlyValAlaLysLysValSerIlePheGlyValLysValLeuAspAspAsn

601
GGCTCGGGCTCGCTCAGCAATGTCATTGCCGGCATGGACTTTGTCGCCCTCTGACTACCGC    660
GlySerGlySerLeuSerAsnValIleAlaGlyMetAspPheValAlaSerAspTyrArg

661
TCTCGCAACTGCCCTCGTGGTGTCGTTGCCAGCATGTCTCTTGGTGGTGGTTACTCGGCC    720
SerArgAsnCysProArgGlyValValAlaSerMetSerLeuGlyGlyGlyTyrSerAla

721
ACCGTGAACCAGGCTGCCGCCCGTCTGCAGTCCTCTCTGGGCGTTCTTTGTCGCTGTCGCCGCT    780
ThrValAsnGlnAlaAlaAlaArgLeuGlnSerSerGlyValPheValAlaValAlaAla

781
GGCAACGACGACAACCGTGATGCTGCCAACACTTCGCCCTCGGAGCCCTCGGTTTGCACC    840
GlyAsnAspAspAsnArgAspAlaAlaAsnThrSerProAlaSerGluProSerValCysThr

841
GTCGGGGCTACTGACTCGTCCGATCGTCGTCGCTCGTCTTTCCAACTATGGTCGTGCCCTT    900
ValGlyAlaThrAspSerSerAspArgArgSerSerPheSerAsnTyrGlyArgAlaLeu

901
GATATTTCGCTCCCGGCACTGACATCACCTCCACCTGATTGGCCGGCACGAACACC    960
AspIlePheAlaProGlyThrAspIleThrSerThrTrpIleGlyTyrGlyArgThrAsnThr
```

FIG. 2c

```
961
ATCTCTGGAACCTCCATGGCTACTCCCCACATTGCTGGTCTCGGTGCCTACCTTCTGGCT
IleSerGlyThrSerMetAlaThrProHisIleAlaGlyLeuGlyAlaTyrLeuLeuAla
                                                          1020

1021
CTCGAGGGTGGCAGTGCCAGCACTATCTGTGCTCGTATCCAGACTCTCTCCACCAAGAAT
LeuGluGlyGlySerAlaSerThrIleCysAlaArgIleGlnThrLeuSerThrLysAsn
                                                          1080

1081
GCCATCTCGGGGCCGTTCCCTCGGGTACCGTCAACTACCTGGCCTTCAACAACGCCACGTGA
AlaIleSerGlyValProSerGlyThrValAsnTyrLeuAlaPheAsnAsnAlaThr***
                                                          1140
```

FIG. 4

Amino acid sequence of peptide a

N Ala-Ile-Thr-Gln-Gln-Gly-

DNA codon of peptide a

```
                T  T  T  A     A  A     T
5' GC C AT C AC C CA G CA G CA G GG C
                A  A  A        A        A
                G  G  G                 G
```

DNA sequence of synthetic probe

```
         C  C  C
5' GC T AT T AC T CAGCAGCAGGG
```

Amino acid sequence of peptide b

N Asp-Ile-Phe-Ala-Pro-Gly-Thr-

DNA codon of peptide b

```
                   T  T  T  T     T     T
5' GA C AT C TT C GC C CC C GG C AC
                      A     A  A  A     A
                            G           G
```

DNA sequence of synthetic probe

```
            A  G  A     A        A
5' GT G CC T GG G GCGAA G AT G TC
```

FIG. 6

| | |
|---|---|
| Upstream of translation initiation site<br>+ strand | 5'-CAAAAACTCACTTCTCAACC-3'<br>(20mer) |
| Downstream of translation termination site<br>- strand | 5'-CCAGCCTTCATGCCTCCAGA-3'<br>(20mer) |

FIG. 13

| | | |
|---|---|---|
| a) Vicinity of APase promoter 5'-terminal + strand | 5'—TAGAGGATCCGAAAGAT—3'<br>           BamH1 | |
| b) Vicinity of APase pro region gene 3'-terminal − strand | 5'—ATAGCATTAATGCTGATGATGGC—3'<br>              Vsp1 | |
| c) Synthetic linker | 5'—TAATAAGGTTTT            —3'<br>3'—         TATTCCAAAAGC—5'<br>      Vsp1            Taq1 | |

DNA CODING FOR ALKALINE PROTEASE

This application is a Rule 62 continuation of now abandoned application, Ser. No. 07/887,284, filed May 22, 1992, now abandoned.

FIELD OF THE INVENTION

The present invention relates to a novel DNA and its use. More specifically, it relates to a structural gene of an alkaline protease (hereinafter sometimes referred to as APase) produced by a mold belonging to the genus Fusarium, a region responsible for its expression and secretion and the production of various proteins utilizing them.

BACKGROUND OF THE INVENTION

Many attempts at mass production of useful proteins utilizing gene recombination techniques have been done by using prokaryotes such as *Escherichia coli, Bacillus subtilis* and the like as hosts, and eukaryotes such as yeast, animal cells and the like. Firstly, techniques for producing and accumulating the desired products in microbial cells have been established, and such techniques have been utilized for the production of useful proteins such as interferons, cytokines, hormones and the like by using *Escherichia coli* or *Bacillus subtilis*. However, when products are accumulated in microbial cells, there are problems that the amount of an accumulated product is limited and, sometimes, only an inactive product is produced. Then, various attempts for production and secretion of products outside of microbial or animal cells have also been done by using *Bacillus subtilis*, yeast, animal cells and the like.

On the other hand, it has been known for long time that molds secrete enzymes in an extremely large amount, and they have been noted as a host for gene recombination. In this respect, production-by-secretion systems using molds belonging to the genera Aspergillus, Trichoderma, Mucor and the like have been reported. However, such systems are not always well established industrially.

In order to establish an efficient production-by-secretion process of proteins, powerful promoters and secretion signals which are operable in a host organism to be used are essential. The efficiency of the promoter and secretion signal varies according to particular kinds of host organisms. Further, the efficiency also varies according to nucleotide sequences of genes coding for the desired proteins or the protein structure. Therefore, powerful new promoters and secretion signals have been under investigation.

OBJECTS OF THE INVENTION

One object of the present invention is to provide a novel DNA fragment useful for producing various useful proteins.

Another object of the present invention is to provide a plasmid containing the novel DNA fragment.

Still another object of the present invention is to provide a microorganism transformed with the plasmid.

Still another object of the present invention is to provide a process for producing a protein by using the transformant.

These objects as well as other objects and advantages of the present invention will be apparent to those skilled in the art from the following description with reference to the attached drawings.

BRIEF EXPLANATION OF THE DRAWINGS

FIGS. 1a to 1d show the nucleotide sequence of an APase gene. In the FIGS. 1a to 1d, the capital letters represent the sequence of the structural gene and the small letters represent the non-translation and intervening sequences.

FIGS. 2a to 2c show the nucleotide sequence of a structural gene coding for APase protein and the corresponding amino acid sequence.

FIG. 4 show the nucleotide sequence of a synthetic probe.

FIG. 6 shows the nucleotide sequence of the synthetic probe used in cloning of cDNA.

FIG. 13 shows the nucleotide sequence of the synthetic primer and synthetic linker used for construction of human lysozyme expression plasmid.

SUMMARY OF THE INVENTION

Figure 3:
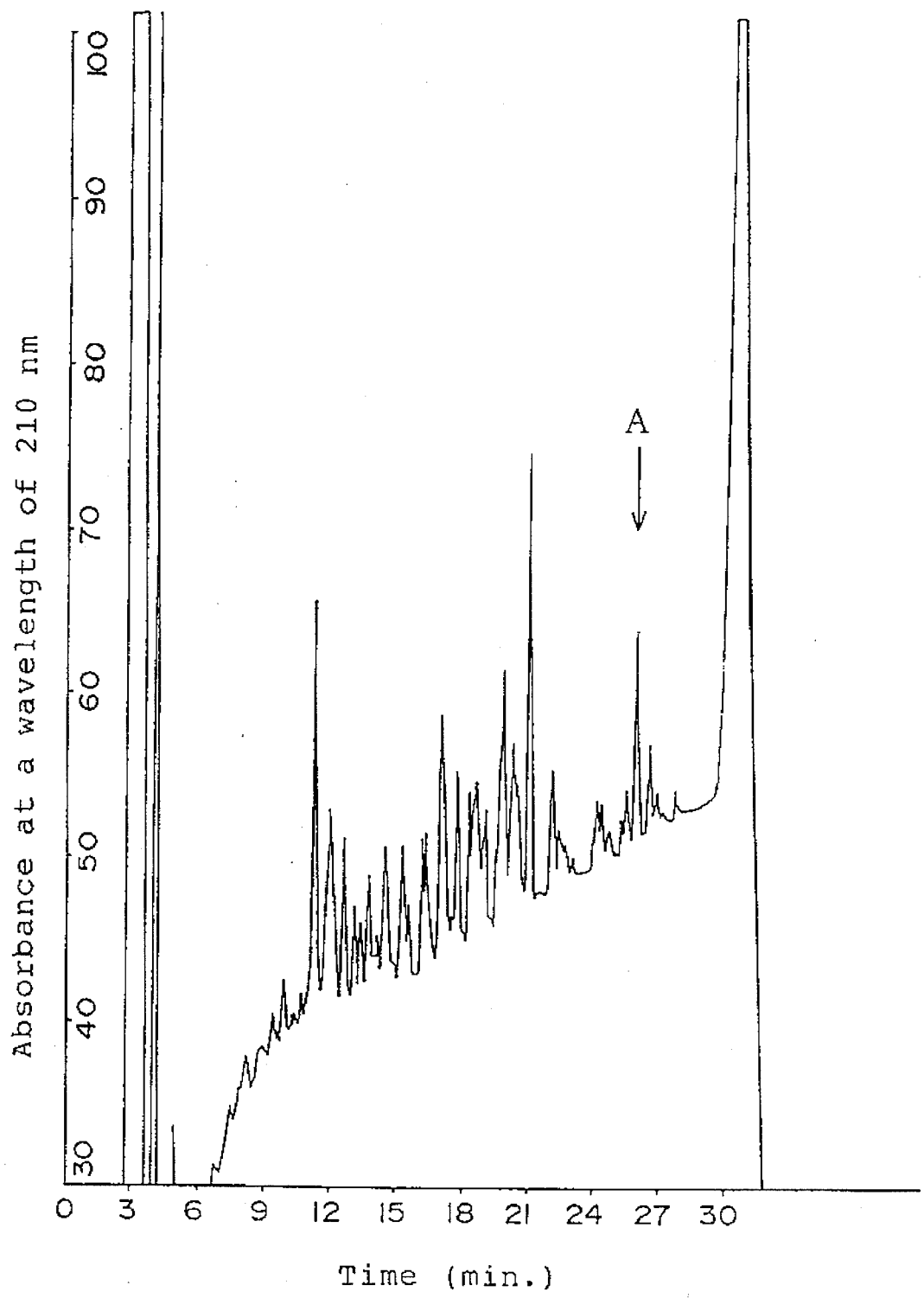
FIG. 3 shows the results of peptide mapping obtained by digestion of APase protein with lysyl endopeptidase.

The present inventors have noted that a mold of the genus Fusarium secretes APase in an extremely large amount [Tomoda et al., Journal of the Takeda Research Laboratories, 38, 33 (1979)], and intensively investigated a gene thereof. As a result, the present inventors have succeeded in cloning of the gene. In addition, the present inventors have succeeded in clarification of the nucleotide sequence of the promoter, translation initiation site and secretion signal thereof. Based on these findings, the present inventors have conducted further studies in order to produce proteins efficiently by using these sequences. Thus, the present invention has been completed.

That is, according to the present invention, there are provided:

(1) A DNA fragment containing a part or all of an alkaline protease gene, (2) A plasmid into which the DNA fragment is integrated, (3) A microorganism transformed with the plasmid, and (4) A process for producing various useful proteins, for example, an alkaline protease, human lysozyme and the like by using the transformed microorganism.

DETAILED DESCRIPTION OF THE INVENTION

In the present invention, a site having promoter activity, a translation initiation site, and a secretion signal of an APase gene of a microorganism of the genus Pusarium as well as DNA containing a structural gene coding for APase can be isolated and collected from cells of a microorganism of the genus Fusarium.

Preferable example of the microorganism of the genus Fusarium include *Fusarium osysporum, Fusarium oxysporum F. batatas, Fusarium oxysporum F. gladioli, Fusarium oxysporum F. lini, Fusarium oxysporum F. neveum, Fusarium oxysporum F. lini vasinfectum, Fusarium solani, Fusarium nivale,* and so forth.

Among these microorganisms of the genus Fusarium, *Fusarium oxygsporum* IFO 4471, *Fusarium nivale* IFO 8510, *Fusarium sp.* S-19-5 (IFO 8884, ATCC 20192) strain and its kabicidin resistant strain 5-128B therefrom [Suzuki et al., Agric. Biol. Chem. 38, 135 (1974)] are more preferred. Especially preferable ones are *Fusarium sp.* S-19-5 and its kibicidin resistant strain 5-128B.

The DNA coding for an APase gene can be obtained from the chromosome of a microorganism of the genus Fusarium. The structural gene without any intron can be obtained as the complementary DNA (cDNA) of a messenger RNA (mRNA). The chromosomal DNA can be prepared from microbial cells by using a know method, for example, the method of U. Rader et al. [Lett. Appl. Microbiol., 1, 17 (1975)] or a modification thereof.

Means for detecting DNA to be used in cloning of a DNA fragment containing an APase gene region from chromosomal DNA or cDNA is not specifically limited and there can be used any means by which the presence of an APase gene can be confirmed on the DNA fragment inserted into a vector plasmid. For example, there are a method utilizing dissolution phenomenon of a casein plate by an enzyme, a method wherein a nucleotide probe is synthesized from a partial amino acid sequence of a purified enzyme and converted into a radioactive labeled probe and then the DNA is detected by hybridization, and the like. Further, in the case that amino acid sequences of two or more different parts of an enzyme protein are clear, the cloning efficiency can be improved by using a longer nucleotide probe obtained according to PCR method [Science, 230, 1350 (1985)].

The host for the cloning is not specifically limited but, normally, *Escherichia coli* is used. More specifically, commercially available *Escherichia coli* (e.g., LE 392 strain) or the like is preferred. As the vector, any vector that can be introduced in the host cells can be used. Preferable examples thereof include plasmid vectors such as pBR322, pUC18, pUC19 and the like, lambda phage vector such as Lambda FIX II (manufactured by Stratagene Cloning System Inc., U.S.A.) and the like. Specifically, commercially available Lambda FIX II or the like can be used.

For inserting the chromosomal DNA fragment into a vector, the chromosomal DNA is cleaved or partially cleaved with an appropriate restriction enzyme. On the other hand, the vector DNA is cleaved with the same restriction enzyme as that used in the cleavage of the chromosomal DNA or with a restriction enzyme that can produce a restriction site which can be ligated with the cleaved chromosomal DNA. Then, both are ligated with a DNA ligase, and the chromosomal DNA fragment is inserted into the vector DNA to form a recombinant DNA.

For introducing the recombinant DNA into a host, any known method can be employed. For example, when a plasmid is used as a vector, the competent cell method is employed. When lambda phage vector is used as a vector, the in vitro packaging method is employed. Specifically, Lambda FIX II into which the chromosomal DNA is integrated is packaged in vitro by using a commercially available in vitro packaging kit, and then an *Escherichia coli* host is infected by the packaged vector to form plaques. For detecting the lambda phage vector containing the desired APase gene, the plaque hybridization method can be employed. The lambda phage is recovered by a conventional method from the plaque which can hybridize with the probe used (a labeled DNA fragment prepared by PCR method). The plaque hybridization operation is repeated by using the recovered lambda phage to isolate the lambda phage vector into which the chromosomal DNA fragment containing APase gene are inserted. The phage DNA is isolated from the lambda phage and cleaved with an appropriate restriction enzyme. Then, the cleaved DNA is subcloned into the plasmid vector. Approximate location and size of the desired gene can be known by testing for whether the subcloned chromosomal DNA is hydridized with the above probe or not.

A series of these fundamental operations are known and described in detail in the literatures (Methods in Enzymol., 68, 1979; Molecular Cloning, 1982).

The nucleotide sequence of DNA coding for an APase gene can be determined according to a known method such as the dideoxy chain termination method (Eichi Soeda et al., "Kakusan Enki Hairetu Ketteihou" p. 61–113, Gakkai Shuppan Center, 1985) and/or Maxam-Gilbert Method or the modification thereof. The APase gene, promoter, translation initiation site and secretion signal in the nucleotide sequence thus determined can be readily known from the analysis. SEQ ID No. 1 in the Sequence Listing attached herein and FIGS. 1a to 1d show the nucleotide sequence of the APase gene derived from *Pusarium sp.* S-19-5 (IFO 8884, ATCC 20192) strain obtained in Example 1 hereinafter. "ATG" which starts from the base number 542 is the translation initiation codon. In the upstream non-translation region thereof, there are "TAAATA" sequence (bas number 430–435) which is similar to "TATA" sequence and "CAAT" sequence (base number 126–129, 195–258) both of which are common to promoters of eukaryotes [Proudfoot, Nature, 279, 376 (1979)]. In view of this, the DNA fragment from base number 1 to the translation initiation codon "ATG" (base number 542) in FIG. 1a can be exemplified as the DNA fragment containing the promoter and translation initiation site of an APase gene. However, in so far as the function of the promoter is maintained, a part of the DNA fragment may be deleted. Further, the nucleotide sequence of the region containing the promoter and translation initiation site can be modified so as to change the function of the promoter and translation initiation site, for example, increase in expression efficiency and such a modified fragment can preferably be used. It is also possible to use a fragment wherein a nucleotide sequence which is not responsible for the function of the promoter and translation initiation site is modified. Furthermore, in order to produce the desired product outside of microbial cells, the secretion signal of APase is ligated downstream of the translation initiation codon in the same reading frame. If necessary, the pro region in a downstream location thereof can be included to enhance secretion efficiency. In addition, the gene encoding a part or all of the APase protein can be included to give, sometimes, higher secretion productivity.

Expression of the desired gene (e.g., structural genes of various proteins, etc.) by using the APase gene promoter and the translation initiation site and/or secretion signal of the present invention can be carried out by matching the site derived from the APase gene with the reading frame of the desired gene to construct a fused protein. The desired gene may be the structural genes of various proteins. Preferable examples of said-proteins include useful enzymes derived from microorganisms (e.g., APase, amylase, lipase, cellulase, etc.); physiologically active proteins derived from animals or human [e.g., interferons (e.g., alpha-interferon, gamma-interferon, etc.), cytokines (e.g., interleukin-2, interleukin-6, colony stimulating factor, etc.), hormones (e.g., insulin, etc.), cell growth factors (e.g., fibroblast growth factor, epidermal growth factor, nerve cell growth factor, etc.), enzymes (e.g., tissue plasminogen activator. lysozyme, urokinase, etc.)].

Among these proteins, useful enzymes derived from microorganisms (e.g., APase, amylase, lipase, cellulase, etc.) and enzymes derived from animals or human (e.g., tissue plasminogen activator, lysozyme, urokinase, etc.) are more preferred. Especially preferable ones are APase and lysozyme.

The gene to be used for expression may be any gene, for example, genes isolated from chromosomes, cDNa obtained from mRNA, chemically synthesized genes, fused genes thereof and the like. However, genes whose nucleotide sequences are clear are preferred. When a fused gene is constructed with the APase gene, a DNA fragment corresponding to a part of amino acids can be removed from the amino terminus in so far as the products of the fused gene maintains the desired activity.

A series of basic operations to fuse these genes are know and described in detail in the literature (Methods in Enzymol., 68, 1979; Molecular Cloning, 1982). When both genes are ligated, chemically synthesized DNA can be used as an adapter DNA between both genes. As the chemically synthesized DNA, any DNA can be used in so far as the frames of both genes match each other and the activities of the desired gene are not lost.

As the host into which the desired gene ligated at the position downstream of the promoter and the region coding for the translation initiation site and/or secretion signal are introduced, any organism whose genes are operable and expressible can be used. Preferably, the host can be appropriately selected from eukaryotes such as yeast, mold, plant and the like. More preferably, the host can be appropriately selected from eukaryotic microorganisms such as yeast, mold and the like. Examples of yeast include those belonging to the genera Saccharomyces, Schizosaccharomyces, Pichia and the like. More specifically, there are *Saccharomyces cerevisiae, Schizosaccharomyces pombe, Pichia pastoris* and the like. Examples of mold include those belonging to the genera Acremonium, Aspergillus, Penicillium, Mucor, Neurospora, Trichoderma and the like. More specifically, there are *Acremonium chrysogenum, Aspergillus niger, Aspergillus oryzae, Aspergillus awamori, Penicillinum chrysogenem, Mucor javanious, Neurospora crassa, Trichoderma viridae* and the like. Among these eukaryotic microorganisms, *Acremonium chrysogenum* is more preferred. Specific examples thereof include *Saccharomyces cerevisiae* AH22R strain, *Acremonium chrysogenum* ATCC 11550 strain and ATCC 14553 strain, *Aspergillus oryzae* IFO 5240 strain, *Aspergillus awamori* IFO 4033 strain, *Mucor javanicus* IFO 4570 strain, *Trichoderma viridae* IFO 31137 strain and the like. Among these strains, *Acremonium chrysogenum* ATCC 11550 is more preferred.

As the transformation method to introduce the gene into these hosts, for example, there is the protoplast transformation method (Winer et al., Microbiology, 1985, 468, American Society for Microbiology). For isolating the transformant efficiently, the fused gene may be inserted into a plasmid containing an appropriate selection marker gene which is operable in the host and then the host may be transformed with the plasmid. As the selection marker gene, any gene can be used in so far as the transformant can selectively be isolated. Examples thereof include hygromycin B resistant gene (JP-A 2-265494).

For the cultivation of the transformant obtained in the present invention, a culture medium containing carbon and nitrogen sources assimilable by the transformant and the like can be used. Any carbon source assimilable by the transformant can be used. Examples thereof include glucose, sucrose, starch, soluble starch, dextrin, glycerin, n-paraffin and the like as well as organic acids (e.g., acetic acid, fumaric acid, benzoic acid, etc.), alcohols (e.g., methanol, ethanol, butanol, etc.), fats and oils (soybean oil, lard, etc.) and the like. They can be used alone or in combination thereof. As the nitrogen sources, there are, for example, peptone, soybean flour, cotton seed flour, meat extract, yeast extract, dried yeast, corn steep liquor, corn gluten meal, urea, ammonium salts (e.g., ammonium chloride, ammonium sulfate, etc.), nitrates (e.g., potassium nitrate, ammonium nitrate, etc.), other organic or inorganic nitrogen-containing materials and the like. They can be used alone or in combination thereof. In addition, inorganic salts (e.g., phosphates, etc.), trace metal salts (e.g., magnesium salt, calcium salt, manganese salt, etc.) can be appropriately added.

In general, the cultivation is advantageously carried out by submerged culture under aerobic conditions. The cultivation is preferably carried out at a temperature of about 15° to 35° C. A better result can be obtained by adjusting pH to about 2 to 10, preferably about 4 to 9. In general, the cultivation is carried out for about 2 to 20 days, preferably about 3 to 14 days, more preferably about 3 to 10 days. The desired product is accumulated in the culture medium and/or the microbial cells.

When the desired product (e.g., the above various proteins) is accumulated in the culture medium, a supernatant fluid containing the desired product can be obtained by centrifugation or filtration. On the other hand, when the desired product is accumulated in the microbial cells, after the cultivation, the cells are collected by a known method and the desired product is recovered by an appropriate method. For example, the cells are suspended in a buffer containing a protein denaturant such as guanidine hydrochloride, the suspension is stirred in a cold place, and then the supernatant fluid containing the desired product is obtained by centrifugation or the like. Alternatively, after the cells are suspended in a buffer, the cells are ground by glass beads, or broken by French press, sonication, enzymatic treatment or the like, and then the supernatant fluid is obtained by centrifugation or the like.

For separation and purification of the objective protein from the above supernatant fluid, per se known separation and purification methods can be appropriately combined. As the known separation and purification methods, there are, for example, a method utilizing a difference in solubilities (e.g., salting out, precipitation with a solvent, etc.), a method mainly utilizing a difference in molecular weights (e.g., dialysis, ultrafiltration, gel filtration, etc.), a method utilizing a difference in charges (e.g., ion exchange chromategraphy, etc.), a method utilizing specific affinity (e.g., affinity chromatography, etc.), a method utilizing a difference in hydrophobicities (e.g., reverse phase high performance liquid chromatography, etc.), a method utilizing a difference in isoelectric points (e.g., isoelectric focusing, etc.) and the like.

The proteins thus purified have biological activities similar to those of known proteins such as natural proteins and the like and can be used for various purposes such as medicaments, food and detergent.

As described hereinabove, the APase gene promoter and/or secretion signal of the present invention can efficiently express and secrete heterogeneous genes by using mold or yeast as a host and therefore they are extremely useful from the industrial viewpoint.

PREFERRED EMBODIMENTS OF THE INVENTION

The following examples further illustrate the present invention in detail but are not to be construed to limit the scope thereof.

EXAMPLE 1

Cloning of APase Genome DNA

1) Preparation of chromosomal DNA of *Fusarium sp.* S-19-5 (IFO 8884) strain

*Fusarium sp.* S-19-5 cells of a stock slant culture were inoculated to a culture medium containing saccharose (3 g/liter), $K_2HPO_4$ (1 g/liter), $NaNO_3$ (2 g/liter), $MgSO_4 \cdot 7H_2O$ (0.5 g/liter), KCl (0.5 g/liter), $FeSO_4 \cdot 7H_2O$ (0.01 g/liter), malt extract (5 g/liter), yeast extract (2.5 g/liter) and Casamino acid (2.5 g/liter), and incubated on a rotary shaker (200 rpm) at 25° C. for 5 to 6 days. The chromosomal DNA (about 3.2 mg) was obtained according to the method of V. Rader et al. [Lett. Appl. Microbiol. 1, 17 (1975)] from the microbial cells obtained by filtrating the culture solution (1 liter).

2) Construction of chromosomal DNA library of *Fusarium sp.* S-19-5 (IFO 8884) strain Portions of the chromosomal DNA (each 80 µg) obtained in the above 1) were reacted with 5 units of the restriction enzyme MboI at 37° C. for 3, 5, 8 and 15 minutes, respectively, to partially digest them and then they were mixed. The mixture was reacted with DNA polymerase I large fragment (manufactured by Takara Shuzo, Kyoto, Japan) in the presence of dATP and dGTP. The resulting fragment was ligated to a XhoI cleavage fragment of phage vector Lambda FIX II, partially filled in the arm (manufactured by Stratagene Cloning System, U.S.A.) by using T4 DNA ligase. The ligation reaction mixture was subjected to in vitro packaging by using GIGAPACK GOLD (manufactured by Stratagene Cloning System, U.S.A.). The titer of the gene library thus constructed was $3.2 \times 10^6$ PFU/µg.

3) Determination of amino acid sequence of peptides constituting APase

For isolating a clone having the desired APase chromosomal DNA from the chromosomal DNA library constructed in the above 2), it is effective to chemically synthesize DNA fragment corresponding to the amino acid sequences at several sites of the APase and to carry out plaque hybridization using a probe prepared by the polymerization chain reaction (PCR) method using the DNA synthesized above as a primer.

The amino acid sequence of a purified APase [See, Journal of The Takeda Research Laboratories, 38, 33 (1979)] was determined from the N-terminus according to the Edman method [Acta. Chem. Scand., 4, 283 (1950)]. The results are shown in Table 1-a. Further, the purified APase ample (180 µg) was dissolved in 0.1M Tris-HCl buffer (pH 8) containing 4M urea, and digested with lysyl endopeptidase (manufactured by Wako Pure Chemical, Osaka Japan) (1 µg) at 30° C. for 8 hours. The lyophilized digestion product was dissolved in 0.1% trifluoroacetic acid and subjected to high performance liquid chromatography using $C_{18}$-ODS column (manufactured by Toso, Japan). Elution was carried out by a linear gradient of acetonitrile (0 to 80%) containing 0.1% trifluoroacetic acid. The fractions corresponding to peak A in the elution pattern shown in FIG. 3 are collected, and then the amino acid sequence was determined from the N-terminus of the peptide by the Edman method [Acta. Chem. Scand., 4, 283 (1950)]. The amino acid sequence containing 10 amino acids was determined as shown in Table 1-b.

TABLE 1

Amino acid sequences of peptide derived from APase

| Peptide | Amino acid sequence |
|---|---|
| a | Ala-Ile-Thr-Gln-Gln-Gln-Gly-Ala-Thr-Trp-Gly-Leu-Thr-Arg-Ile-Ser-His-Arg-Gln-Arg-(SEQ ID NO. 3) |
| b | Asp-Ile-Phe-Ala-Pro-Gly-Thr-Asp-Ile-Thr-(SEQ ID NO. 4) |

4) Preparation of APase genome DNA screening probe

DNA shown in FIG. 4 corresponding to the amino acid sequences determined in the above 3) were synthesized chemically. PCR was carried out by using both DNA (1 µM) as primers and the chromosomal DNA (1 µg) obtained in the above 1) as a template according to the method described in Gene Amplification Kit (manufactured by Perkin-Elmer Cetus Inc., U.S.A.) using Tag DNA polymerase. The gene was amplified with DNA Thermalcycler PJ2000 (manufactured by Perkin-Elmer Cetus Inc.) by 35 cycles of 94° C. for 1 minute, 55° C. for 2 minutes and 72° C. for 1.5 minutes, and subjected to electrophoresis on agarose gel (2%) (see, Molecular Cloning, p. 150–162, 1982) to obtain a probe DNA (700 bp).

5) Cloning of APase genome DNA from the chromosomal DNA library

The gene library constructed in the above 2) was diluted so that 20 thousand plaques per plate appeared. Then plaques were allowed to appear by using *Escherichia coli* LE 392 strain as an indicator microorganism. The plaques were lifted on a colony/plaque screen (manufactured by NEM Research Products, U.S.A.). The DNA probe obtained in the above 4) was radiolabeled with $^{32}$P by using a random primer DNA labeling kit (manufactured by Takara Shuzo, Kyoto Japan) according to the description of Appl. Biochem., 137, 266 (1984) and plaque hybridization (see, the above Molecular Cloning, pp. 326–238) was carried out with the $^{32}$P radioactive labeled probe DNA obtained in the above 4) at 65° C. for 24 hours in a hybridization solution containing 1% SDS, 1M saline, 10% dextran sulfate and 100 µg/ml of heat denatured salmon sperm DNA. Lambda-DNA was separated from a positive plaque which was found to be hybridized with the probe by using Lambda Solve Adsorbent (manufactured by Promega, U.S.A.).

6) Subcloning of APase genome DNA

DNA obtained in the above 5) was cleaved with the restriction enzyme BamHI and then BamHI fragment (3.1 kbp) was isolated by agarose gel electrophoresis (see, the above Molecular Cloning, pp. 150–162). On the other hand, phage vector M13 was cleaved with the restriction enzyme BamHI. Two DNA fragments thus obtained were mixed and ligation reaction was carried out by using T4 DNA ligase. *Escherichia coli* JM 109 strain was transformed with this ligation reaction mixture to obtain plasmid MNG-1 (see, FIG. 5) in which the BamHI fragment (3.1 kbp, containing the APase gene of *Fusarium sp.* S-19-5 strain) was inserted into the BamHI site of M13.

EXAMPLE 2

Nucleotide Sequence of APase Genome DNA

The base sequence of BamHI fragment (3.1 Kbp) containing APase genome DNA of *Fusarium sp.* S-19-5 strain was determined according to the dideoxy chain termination method (see, Eichi Soeda et al., Kakusan no Enki Hairetsu Kettei-hou, pp. 61–113, Gakkai Shuppan Center, 1985). The results are shown in SEQ ID No. 1 in the attached Sequence Listing and FIGS. 1a to 1d.

EXAMPLE 3

Cloning of APase cDNA

1) Obtaining mRNA

Entire RNA (about 2.6 mg) was obtained according to the method of J. M. Clements et al. [Curr. Genet., 9, 293 (1985)] from the microbial cells (2 g) obtained in the same manner as that described in above Example 1-1). Namely, microbial cells powdered under freezing with liquid nitrogen in a mortar were suspended in an extraction buffer (10 ml) containing 4M guanidine thiocyanate, 0.1M Tris-HCl (pH 7.5), 1% 2-mercaptoethanol and 0.5% SDS. A solution of 5.7M cesium chloride containing 4 mM EDTA (pH 7.5) was placed in a polyaroma centrifugal tube (5 ml). The suspension was layered over the solution and was centrifuged at 30,000 rpm at 20° C. for 23 hours by using SW 41 rotator (manufactured by Beckman, U.S.A.). After centrifugation, RNA was recovered according to ethanol precipitation method. Preparation of mRNA was carried out according to the method described in Fast Track mRNA isolation kit (manufactured by Invitrogen, U.S.A.) to obtain mRNA (4.2 µg) from the above-obtained entire RNA (2.6 mg).

2) Synthesis of cDNA cDNA was synthesized by using cDNA synthesis system plus (manufactured by Amasham Inc., U.S.A.). Synthesis of cDNA was carried out by using mRNA (4.2 µg) obtained in the above 1) according to the method described in Mol. Cell. Biol., 2, 161 (1982) and Gene, 25, 263 (1983) to obtain double-stranded DNA (340 ng).

3) Cloning of APase cDNA

For isolation of the desired APase cDNA from the cDNA mixture obtained in the above 2), it is effective to chemically synthesize DNA in the vicinity of the translation initiation site and the translation termination site estimated from APase genome DNA nucleotide sequences, followed by carrying out PCR for the cDNA template using the chemically sinthesized DNA as a primer to amplify APase cDNA.

Figure 7:
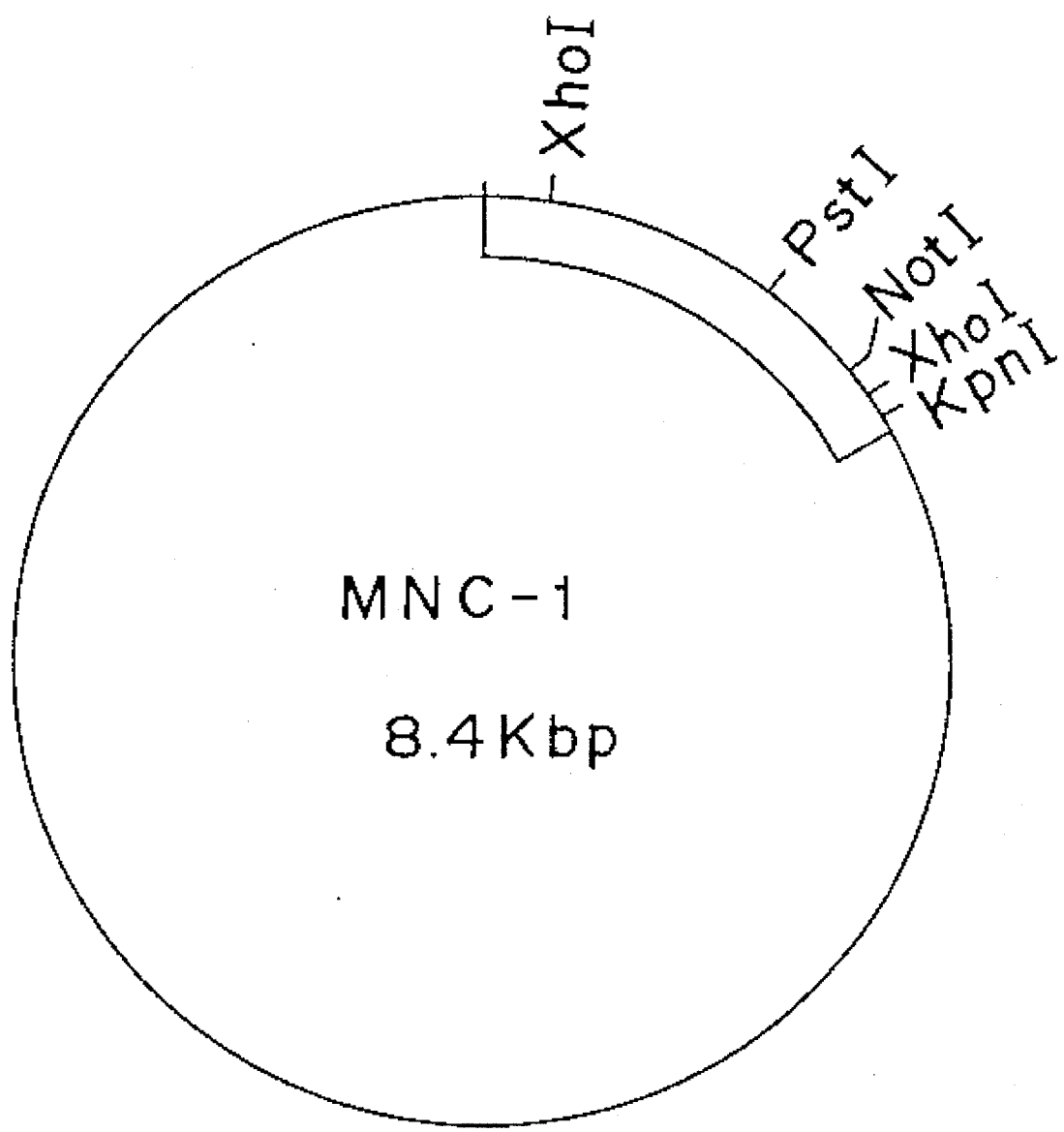
FIG. 7 shows the structure of plasmid MNC-1 into which APase cDNA is inserted.

Firstly, DNA shown in FIG. 6 which was estimated from the APase genome DNA nucleotide sequence shown in FIGS. 1a to 1d was synthesized chemiclaly. PCR was carried out according to the method described in Gene Amplification Kit (manufactured by Perkin-Elmer Cetus Inc.) with Taq DNA polymerase by using the DNA (1 µM) thus synthesized as a primer and the cDNA (3.4 µg) obtained in the above 2) as a template. The gene was amplified by 35 cycles of 94° C. for 1 minute, 55° C. for 2 minutes and 72° C. for 1.5 minutes using DNA Thermal Cycler PJ2000 (manufactured by Perkin-Elmer Cetus Inc.). Then, agarose gel (2%) electrophoresis (see, the above Molecular Cloning, 150–162) was carried out to isolate APase cDNA (1.1 Kbp). APase cDNA (1.1 kbp) thus obtained was phosphorylated with T4 polynucleotide kinase (manufactured by Takara Shuzo, Kyoto Japan), and then was mixed with phage vector M13 cleaved with a restriction enzyme SmaI and ligation reaction was carried out by using T4 DNA ligase. *Escherichia coli* JM 109 strain was transformed with the ligation reaction mixture to obtain a plasmid MNC-1 (see, FIG. 7) in which APase cDNA (1.1 Kbp) was inserted into SmaI site of M13.

EXAMPLE 4

Nucleotide Sequences of APase cDNA

Base sequence of the DNA fragment (1.1 Kbp) containing APase cDNA of *Fusarium sp.* S-19-5 strain were determined according to the dideoxy chain termination method (Eichi Soeda et al., Kausan no Enkihairetsu Ketteihou, pp. 61–113, Gakkai Shuppan Center, 1985). The DNA nucleotide sequence thus determined and amino acid sequence of APase estimated therefrom are shown in SEQ ID No. 2 in the attached Sequence Listing and FIGS. 2a to 2c. Misreading of cDNA by Taq DNA polymerase estimated from the genome DNA nucleotide sequence was corrected by using site-specific mutagenesis system Mutan-K (manufactured by Takara Shuzo, Japan) according to Kunkel method [see, Methods in Enzymology, 154, 367 (1987)].

EXAMPLE 5

Expression of APase Genome DNA in *Acremonium chrysogenum* ATCC 11550 Strain

Figure 8:
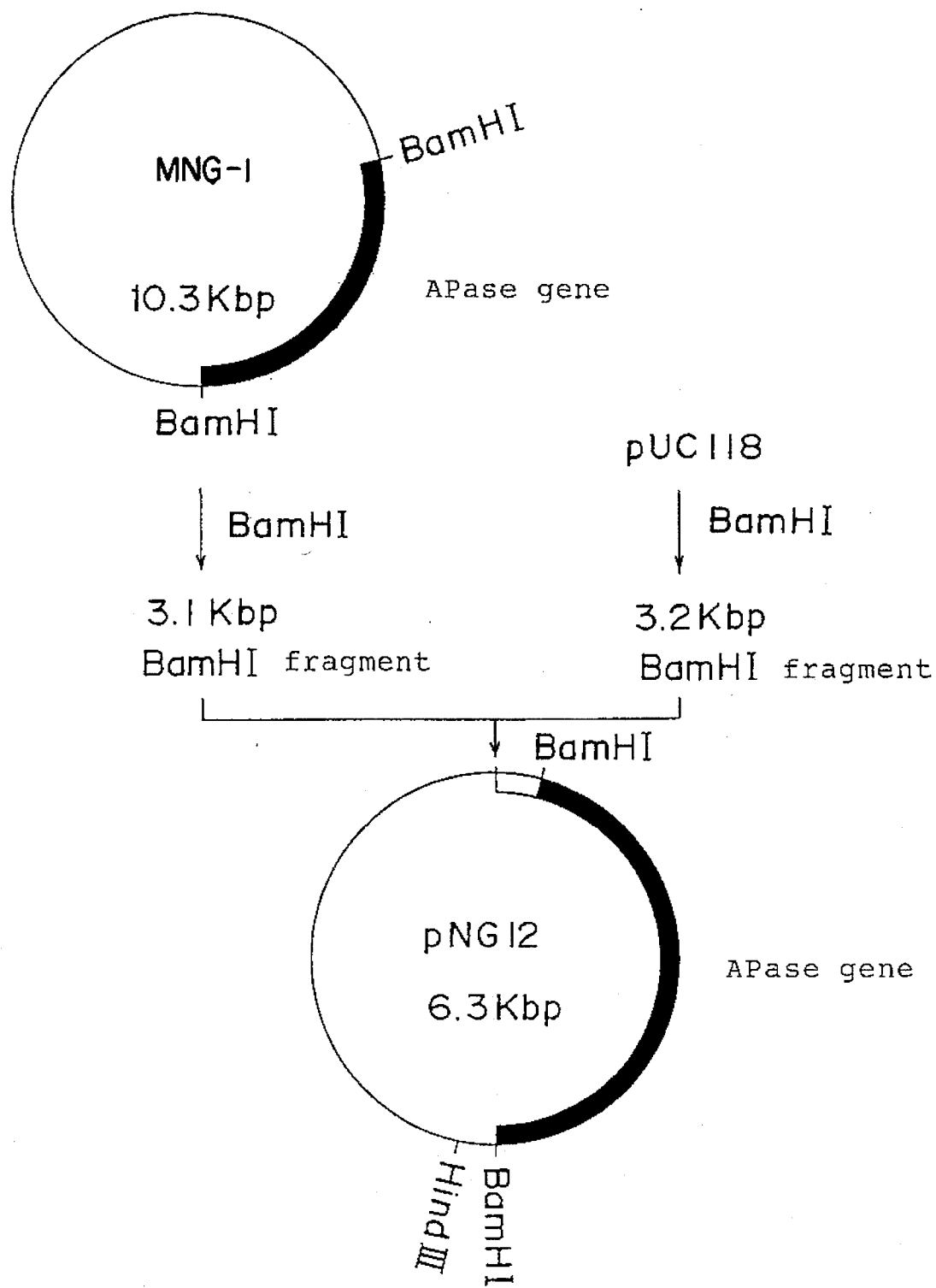
FIG. 8 shows construction of expression plasmid of the APase gene.

1) Construction of plasmid pNG 12 (see, FIG. 8)

Figure 5:
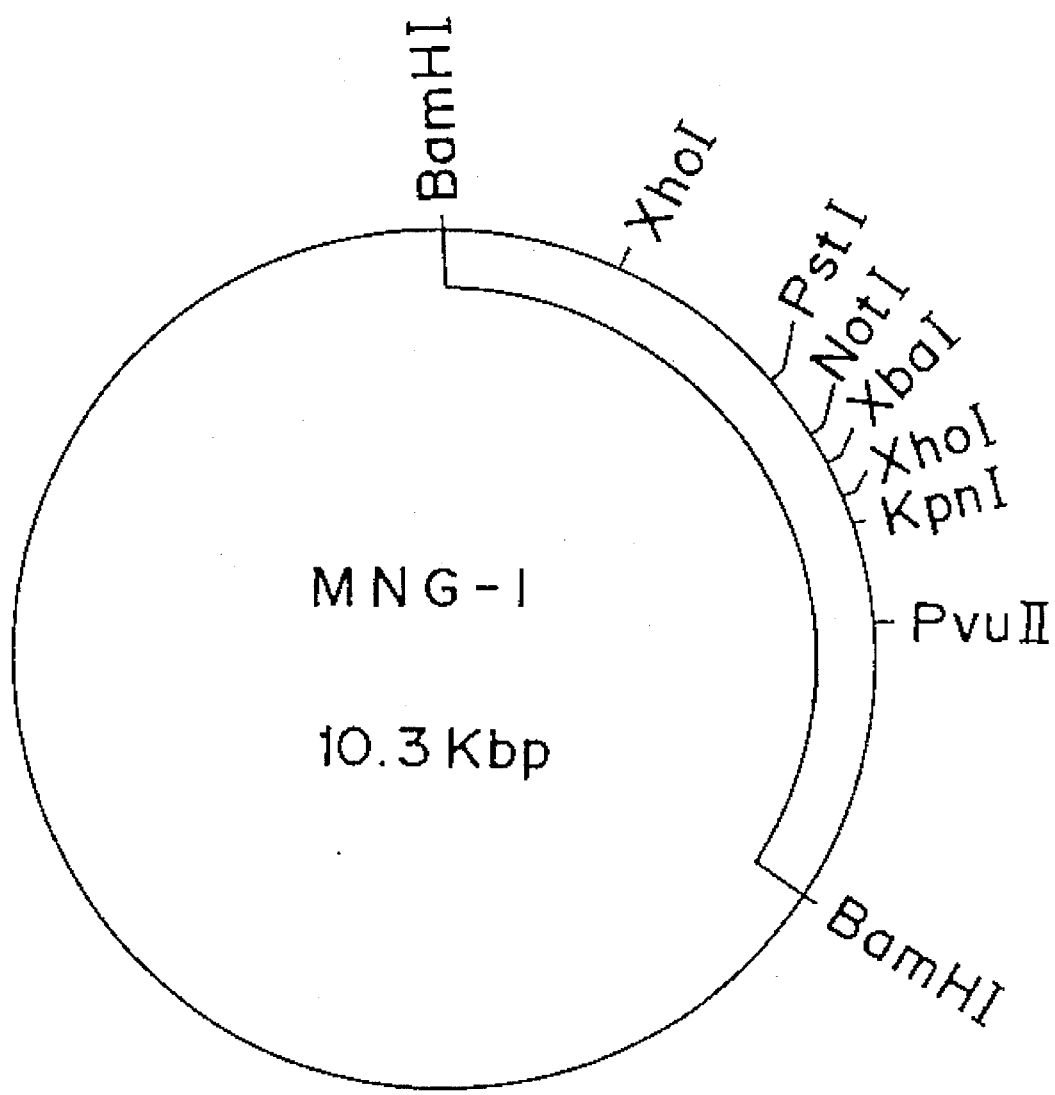
FIG. 5 shows the structure of plasmid MNG-1 containing a cloned APase gene.

Plasmid MNG-1 shown in FIG. 5 was cleaved with BamHI and then a BamHI fragment (3.1 Kbp) was isolated by agarose gel (0.7%) electrophoresis (see, the above Molecular Cloning, pp. 150–162). Then, the vector plasmid pUC 119 was cleaved with BamHI to prepare a BamHI fragment (3.2 Kbp). These 3.1 Kbp BamHI fragment and 3.2 Kbp BamHI fragment were ligated by using T4 DNA ligase to construct plasmid pNG12.

Figure 9:
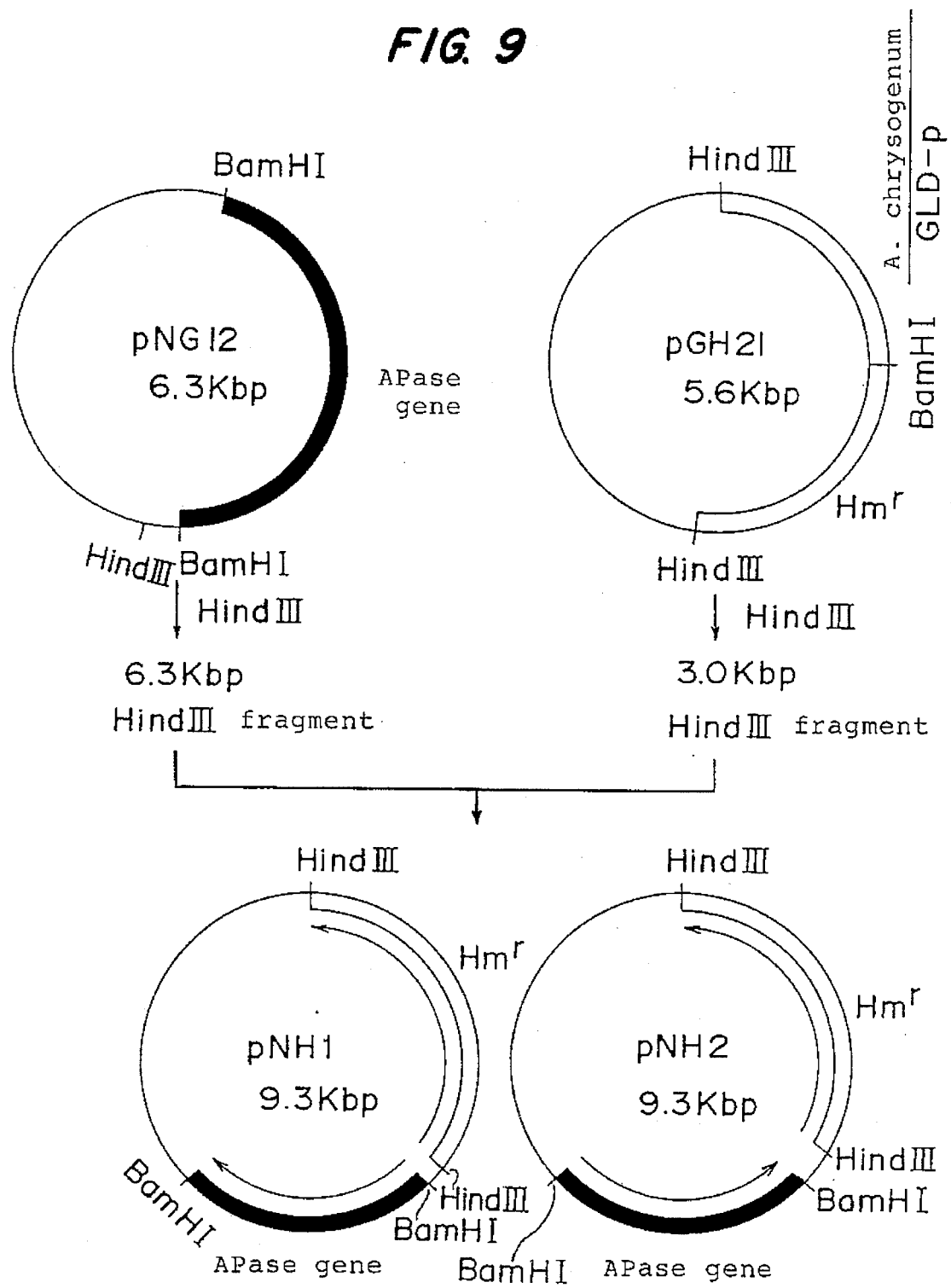
FIG. 9 shows construction of expression plasmid of the APase gene.

2) Construction of plasmid pNH1 and pNH2 (see, FIG. 9)

The plasmid pNG12 obtained in the above 1) was cleaved with HindIII to prepare HindIII fragment (6.3 Kbp). Then, the plasmid pGH21 (see, JP-A 2-265494) in which Hygromycin B. phosphotransferase gene was inserted into the downstream of GLD promoter of *Acremonium chrysogenum* was cleaved with HindIII. Then, a HindIII fragment containing *Acremonium chrysogenum* GLD promoter (3.0 Kbp) and Hygromycin B phosphotransferase was isolated by agarose gel (0.7%) electrophoresis. These 6.3 Kbp HindIII fragment and 3.0 Kbp HindIII fragment were ligated by using T4 DNA ligase to construct plasmids pNH1 and pNH2.

3) Preparation of protoplast from *Acremonium chrysogenum* ATCC 11550 strain

Conidia ($1 \times 10^9$) of *Acremonium chrysogenum* ATCC 11550 strain stored in a frozen state were inoculated to a liquid medium (pH 7.0) containing saccharose (30 g/liter), meat extract (15 g/liter), corn steep liquor (5 g/liter) and β-cyclodextrin (10 g/liter), and incubated on a rotary shaker (200 rpm) at 28° C. for 18 hours. The microbial cells obtained by filtering the culture solution (200 ml) was washed with sterilized water, and then suspended in Macllvaine buffer (13.5 mM citric acid-174 mM sodium phosphate, pH 7.3) (60 ml) containing 0.01M dithiothreitol. The suspension was shaken gently at 28° C. for 15 minutes. The microbial cells were filtered, washed and then suspended in MacIlvaine buffer (60 ml) containing Novozyme 234 (Nove Bio Laboratories, Denmark) (5 mg/ml) and 0.7M NaCl. The cell suspension was shaken gently at 28° C. for 3 hours, and then the protoplasts were separated from the hypae by a glass filter (11G-1). The filtrate was centrifuged (1,000 G, 5 minutes) to precipitate the protoplasts. The protoplasts were washed twice with 0.7M NaCl containing 0.02M $MgSO_4$, and were suspended in 0.7M NaCl so that concentration of the protoplasts were $1 \times 10^8$/ml.

4) Transformation of protoplasts with pNH1 and pNH2

Each of the plasmids pNH1 and pNH2 (10 μg) was added to the protoplast solution (0.1 ml) and mixed lightly. Then 0.7M NaCl (0.4 ml) and 0.05M glycine buffer (pH 7.5) (0.5 ml) containing 36% PEG 4000 (manufactured by Wako Pure Chemical, Osaka Japan) and 106 nM $CaCl_2$ were added and mixed lightly. The mixture was allowed to stand at room temperature for 10 minutes, and then 0.7M NaCl (5 ml) was added and centrifuged (1,000 G, 5 minutes). The precipitated protoplasts were suspended in 0.7M NaCl (0.5 ml) again. The transformed protoplast suspension (0.1 ml) was spread on a plate containing a protoplast regeneration medium [trypticase soy agar (manufactured by Becton Deckinson & Co., U.S.A.) (20 ml) containing 10.8% saccharose] and incubated at 15° C. for 20 hours, and then the plate was over laied with the protoplast regeneration medium (kept at 45° C.) containing Hygromycin B (250 μg/ml). The cultivation was carried out at 25° C. for 5 to 10 days to select the resultant Hygromycin B resistant transformants, *Acremonium chrysogenum*/pNH1 and *Acremonium chrysogenum*/pNH2 [IFO 32394, FERM BP-3400, deposited at Fermentation Research Institute (FRI), Japan under Budapest Treaty as of May 14, 1991] in which pNH1 and pNH2 were inserted into *Acremonium chrysogenum* ATCC 11550 strain, respectively.

5) Cultivation of Hygromycin B resistant transformant

The Hygromycin B resistant transformant obtained in the above 4) was inoculated to SBF medium (saccharose 30 g/liter, DL-methionine 5 g/liter, soybean flour 32 g/liter, $CaCO_3$ 1.5 g/liter, pH 6.8) and incubated on a rotary shaker (250 rpm) at 28° C. for 5 days. The culture solution was centrifuged at 15,000 rpm for 5 minutes, and APase activity in the resulting supernatant was determined by an enzymatic method [see, Agric. Biol. Chem., 38, 135 (1974)]. The results are shown in Table 2. As seen from Table 2, an extremely large amount of APase was accumulated in the medium.

TABLE 2

| Strain | Plasmid | Enzymatic activity |
|---|---|---|
| *Acremonium chrysogenum* ATCC 11550 | none | 200 |
| *Acremonium chrysogenum* ATCC 11550 | pNH1 | 22,800[1] |
| *Acremonium chrysogenum* ATCC 11550 | pNH2 | 25,000[2] |
| *Fusarium sp.* S-19-5 | none | 2,360 |

Note:
[1] *Acremonium chrysogenum*/pNH1
[2] *Acremonium chrysogenum*/pNH2

6) Isolation and purification of APase

The culture solution of *Acremonium chrysogenum*/pNH2 (IFO 32394, FERM BP-3400) obtained in the above 5) was centrifuged to obtain 1 liter of a supernatant. Ammonium sulfate (0.6 saturation) was added to the supernatant and the resultant precipitate was collected by centrifugation. The precipitate was dissolved in cold water (about 100 ml) and dialyzed against 0.01M Tris-HCl buffer (pH 9.0). The dialyzed fluid was passed through DEAE Toyopearl 650M (manufactured by Tosoh, Tokyo Japan) column equilibrated with the same buffer, and the passed liquid was collected. The liquid was dialyzed against 0.02M acetic acid buffer (pH 5.0). Then, the dialyzate was applied onto CM Toyopearl 650M (manufactured by Tosoh) equilibrated with the same buffer. The column was washed with the same buffer and the absorbates were eluted with a linear gradient of NaCl (0 to 0.4M) to obtain an active fraction. The active fraction was dialyzed against water, desalted, lyophilized to obtain a purified enzyme (1.2 g). The enzyme thus obtained was subjected to SDS-polyscrylamide gel electrophoresis to give a single band. This location of migration was confirmed to be identical with that of the standard sample obtained from a culture solution of *Fusarium sp.* S-19-5 strain.

7) Mass production of APase by jar Fermenter cultivation

Figure 10:
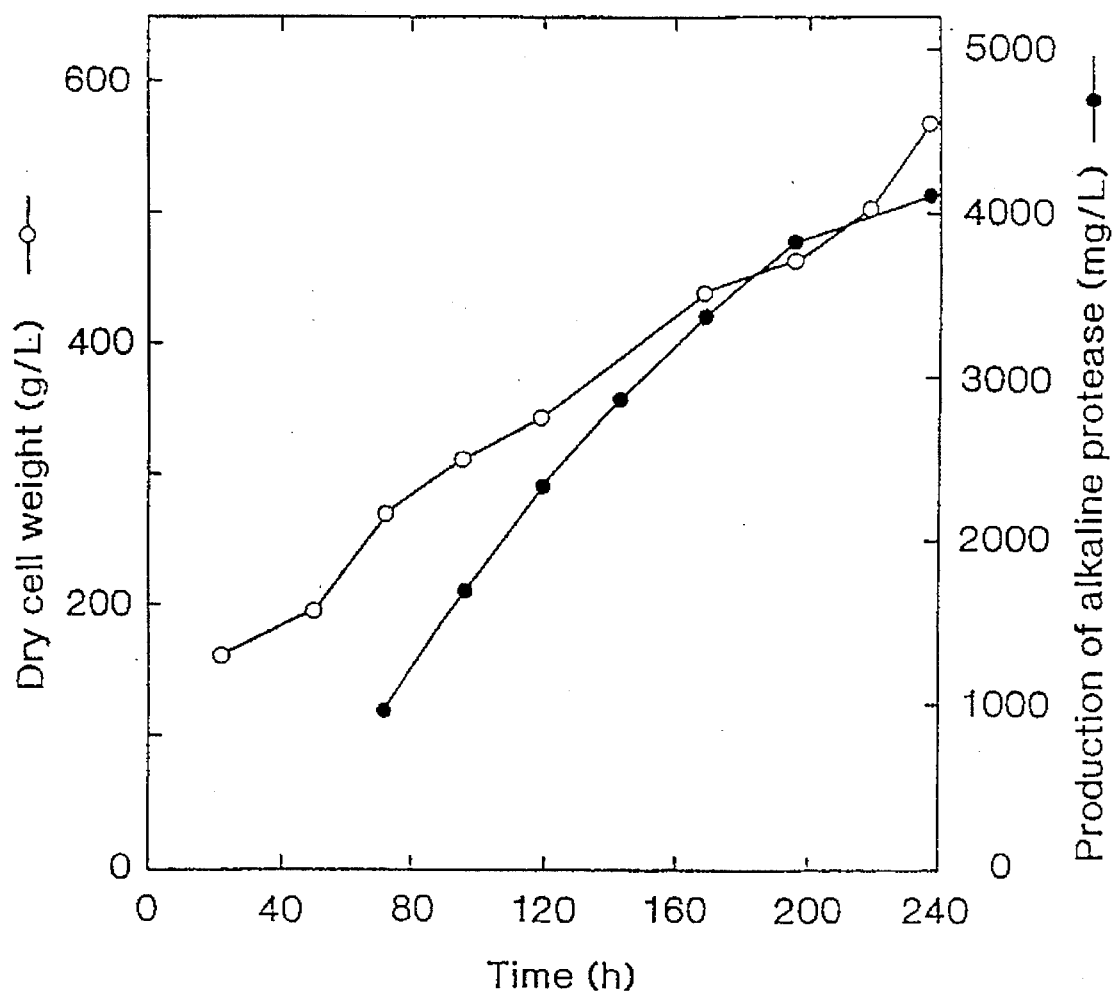
FIG. 10 is a graph showing the relation between the incubation time and the production of APase by *Acremonium chrysogenum*/pNH2 using a jar fermenter.

*Acremonium chrysogenum*/pNH2 (IFO 32394, FERM BP-3400) obtained in the above 5) was inoculated in SBF medium (saccharose 30 g/liter, DL-methionine 5 g/liter, raw soybeam flour 32 g/liter, $CaCO_3$ 1.5 g/liter, pH 7.0) and incubated with aeration and agitation (500 rpm) in a 2 liter jar fermenter at 28° C. for 7 days. Portions of the culture solution (each 10 ml) were collected with time and centrifuged at 15,000 rpm for 5 minutes. The APase activity of the resultant supernatant was determined by the enzymatic method [Agric. Biol. Chem., 38, 135 (1974)]. The amount of the enzyme was calculated from the specific activity of the purified enzyme (5,800 U/mg). Further, the growth of the microorganism was determined by weighing the microbial cells completely dried after centrifugation to obtain the cell weight. As a result, an extremely large amount of APase was accumulated in the medium as shown in FIG. 10.

EXAMPLE 6

Expression of APase cDNA in *Saccharomyces cerevisiae*

Figure 11:
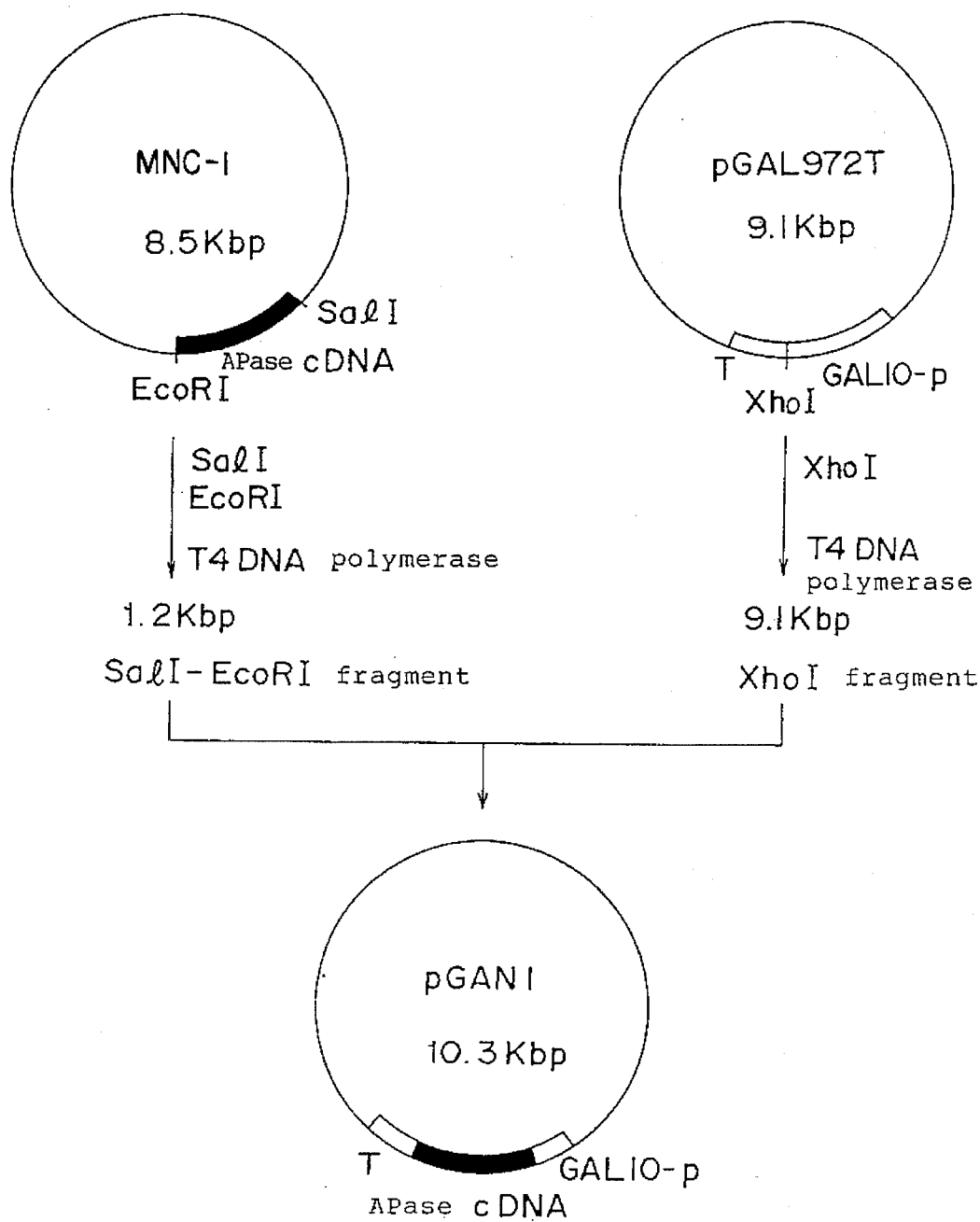
FIG. 11 shows construction of expression plasmid of the APase gene in yeast.

1) Construction of plasmid pGAN-1 (see, FIG. 11)

Plasmid MNC-1 was cleaved with EcoRI and SalI and was isolated by agarose gel (2%) electrophoresis. The fragment was treated with T4 DNA polymerase (manufactured by Takara Shuzo) to obtain a EcoRI-SalI fragment (1.2 Kbp) containing APase cDNA with flush ends. Then, plasmid pGAL972-T having *Saccharomyces cerevisiae* GAL 10 promoter, PGK terminator and LEU2 gene as a selection marker was cleaved with XhoI, and then the resulting fragment was treated with T4 DNA polymerase (manufactured by Takara Shuzo) to obtain a XhoI fragment (9.1 Kbp) having flush ends. These 1.2 Kbp and 9.1 Kbp fragments were ligated together with T4 DNA ligase to construct plasmid pGAN1.

2) Transformation of *Saccharomyces cerevisiae* AH22R-2075 strain with plasmid pGAN1

*Saccharomyces cerevisiae* AH22R⁻-2075 strain was used as a host. *Saccharomyces cerevisiae* AH22R⁻-2075 strain is α type of conjugation has low protease productivity and lacks histidine synthesis gene (his4) and leucine synthesis gene (leu2) [see, Gene, 78, 297 (1989)]. Therefore, the strain cannot be grown unless histidine and leucine are added to the culture medium.

*Saccharomyces cerevisiae* AH22R⁻-2075 was cultivated with shaking at 30° C. for 24 hours in YPD medium (yeast extract 10 g/liter, Bacto trypton 20 g/liter, glucose 20 g/liter)

(50 ml) and was centrifuged to obtain the microbial cells. The cells were transformed with the plasmid pGAN1 obtained in the above 1) according to the method described in Methods in Yeast Genetics, Cold Spring Harbon Laboratory, pp. 121–122 (1981). The transformed yeast suspension (0.1 ml) was spread on YNB agar medium (yeast nitrogen base 6.7 g/litter, glucose 20 g/liter, adenine 30 mg/liter, uracil 30 mg/liter) containing histidine (100 mg/liter) and incubated at 30° C. for 4 to 6 days. The resulting transformant which did not require leucine was selected.

3) Cultivation of leucine non-requiring transformant

The leucine non-requiring transformant obtained in the above 2) was inoculated to a medium containing saccharose (80 g/liter), L-asparagine (5 g/liter), potassium chloride (2 g/litter), potassium dihydrogen phosphate (400 mg/liter), potassium iodide (100 µg/liter), L-histidine (300 mg/liter), glucose (2.5 g/liter), galactose (45 g/liter), magnesium sulfate (500 mg/liter), calcium chloride (330 mg/liter), iron (II) sulfate heptahydrate (10 mg/liter), zinc sulfate (10 mg/liter), manganese sulfate (10 mg/liter), 1M Tris-maleic acid buffer (pH 6.5) (25 ml) and a vitamin solution (2 ml) [inositol (30 g/liter), thiamine hydrochloride (600 mg/liter), calcium pantothenate (600 mg/liter), pyridoxine hydrochloride (600 mg/liter), nicotinic acid (600 mg/liter) and D-biotin (6 mg/liter)], and incubated on a rotary shaker (200 rpm) at 30° C. for 4 days. The culture solution was centrifuged at 15,000 rpm for 5 minutes. The APase activity of the resulting supernatant was determined by the enzymatic method [see, Agric. Biol. Chem., 38, 135 (1974)]. The enzyme (100 mg/liter) was accumulated. The enzyme was isolated from the filtrate of the culture according to the same manner as that described in Example 5-6) to obtain APase (120 mg). As shown in this Example, it was apparent that the signal sequence and/or pro-sequence of APase functioned even in yeast in view of normal secretion of APase to the outside of the microbial cells.

EXAMPLE 7

Secretion of Human Lysozyme in *Acremonium chrysogenum* ATCC 11550 Strain

Figure 12:
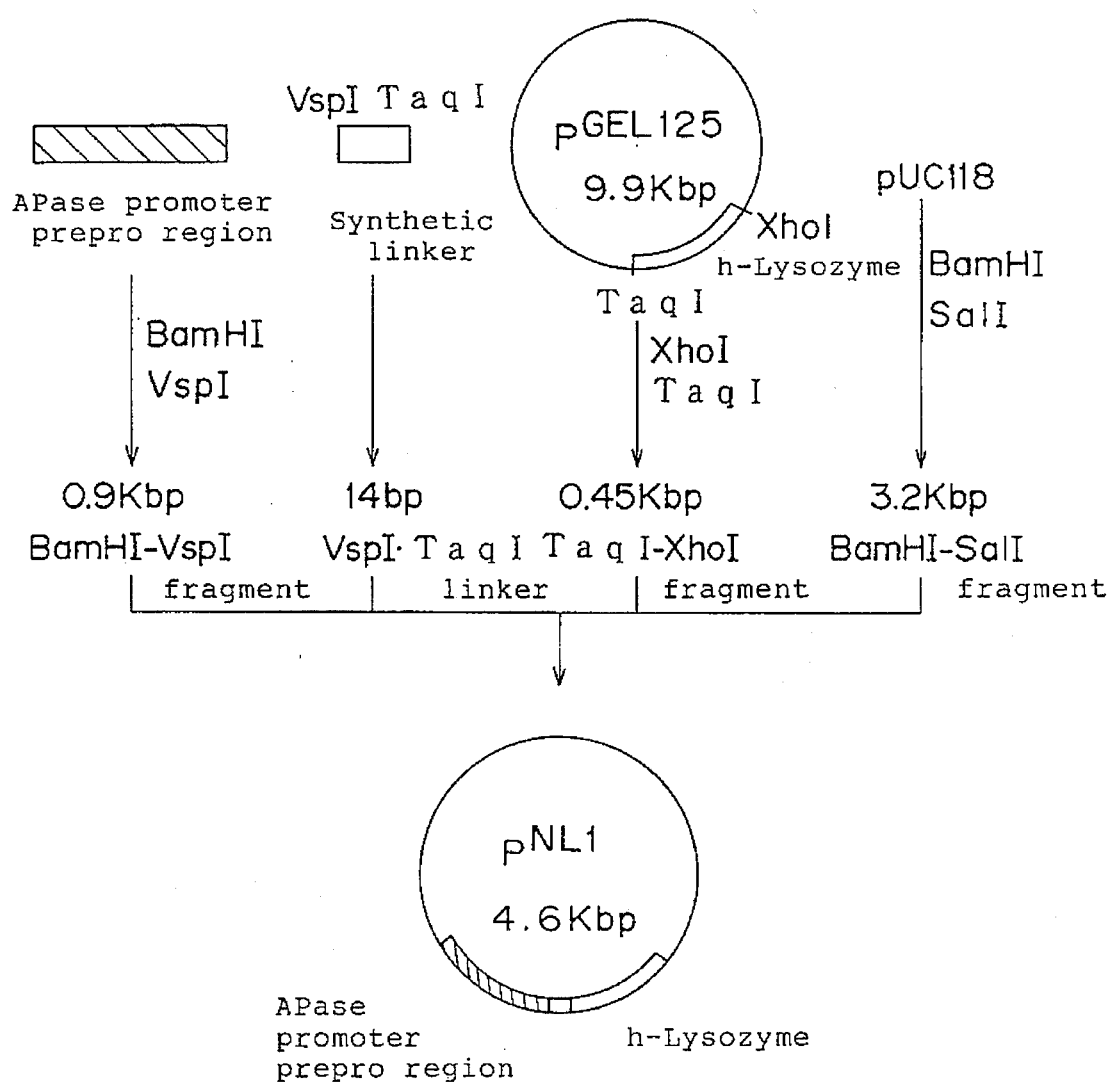
FIG. 12 shows construction of human lysozyme expression plasmid pNL1.
Figure 14:
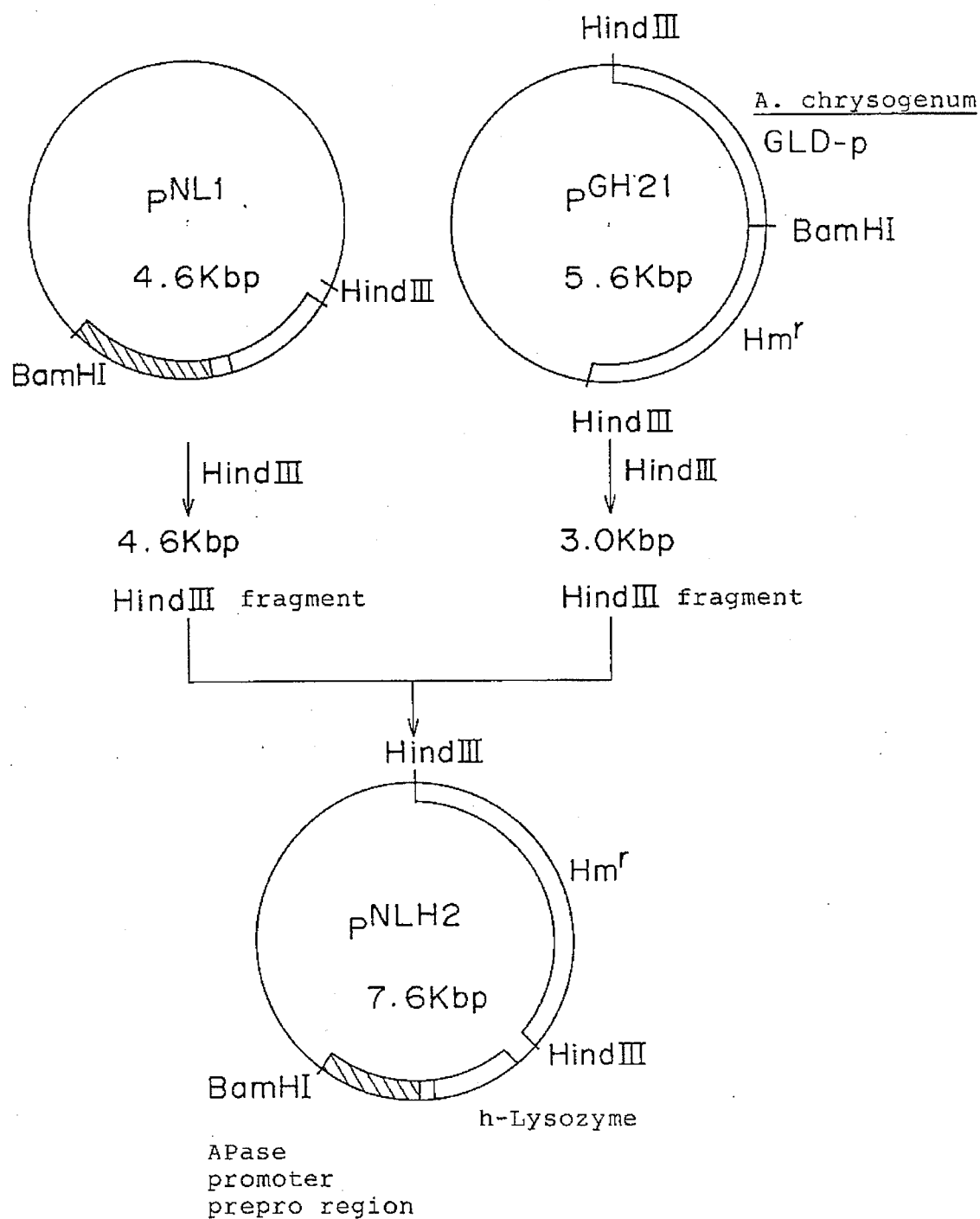
FIG. 14 shows construction of human lysozyme expression plasmid pNLH2.

1) Construction of plasmid pNL1 (see, FIG. 12)

DNA fragments in the vicinity of the APase promoter 5'-terminal and pro-sequence gene 3'-terminal as shown in FIG. 13 a and b were synthesized chemically based on the DNA nucleotide sequence of the APase genome as shown in FIGS. 1a and 1d. The gene was amplified by 35 cycles of 94° C. for 1 minute, at 55° C. for 2 minutes and at 72° C. for 1.5 minutes with the Gene Amplification Kit (manufactured by Perkin-Elmer Ceuts Inc.) by using Taq DNA polymerase and the above-synthesized DNA (1 µM) as a primer and the plasmid pNH1 (1 ng) shown in FIG. 9 as a template. Then, the gene was subjected to agarose (2%) gel electrophoresis (see, Molecular Cloning, p. 150–162, 1982) to isolate DNA (900 bp) corresponding to APase promoter and pre and pro-sequences. The DNA was cleaved with the restriction enzymes BamHI and VspI.

On the other hand, the plasmid pGEL125 into which human lysozyme gene was inserted [see, Biochem. Biophys. Res. Commun., 145, 712 (1987)] was cleaved with XhoI and TagI and then subjected to agarose (2%) gel electrophoresis (see, Molecular Cloning, p. 150–162, 1982) to isolate TagI-XhoI fragment (450 bp) containing human lysozyme gene. Further, the vector plasmid pUC118 was cleaved with BamHI and SalI to prepared BamHI-SalI fragment (3.2 Kbp).

These BamHI-VspI fragment, TagI-XhoI fragment and BamHI-SalI fragment were ligated through the chemically synthesized DNA linker as shown in FIG. 13c by using T4 DNA ligase to obtain the plasmid pNL1.

2) Construction of plasmid pNLH2 (see, FIG. 15)

The plasmid pNL1 obtained in the above 1) was cleaved with HindIII to prepare HindIII fragment (4.6 Kbp).

On the other hand, the plasmid pGH21 as described in Example 5-2) was cleaved with HindIII and then subjected to agarose (0.7%) gel electrophoresis (see, Molecular Cloning, p. 150–162, 1982) to isolate HindIII fragment (3.0 Kbp) containing the GLD *Acremonium chrysogenum* promoter and hygromycinphospho-transferase gene.

These 4.6 Kbp and 3.0 Kbp HindIII fragments were ligated by using T4 DNA ligase to obtain the plasmid pNLH2.

3) Transformation of protoplast with plasmid pNLH2

According to the same manner as that described in Example 5-3) and 4), *Acremonium chrysogenum* ATCC 11550 strain was subject to protoplast transformation by using the plasmid pNLH2 to obtain 10 strains of hygromycin B resistant transformants.

4) Cultivation of hygromycin B resistant transformant

The hydromycin B resistant transformants obtained in the above 3) were inoculated into modified SBF medium (saccharose 100 g/liter, DL-methionine 5 g/liter, soybeam flour 32 g/l, meat extract 10 g/liter, $CaCO_3$ 5 g/liter, $NH_4Cl$ 5 g/liter, pH 7.0) and incubated on a rotary shaker (200 rpm) at 28° C. for 5 days. The culture solution was centrifuged at 15,000 rpm for 5 minutes. The lysozyme activity of the resulting supernatant was determined by an enzymatic method [Biochem. Biophys. Res. Commun, 145, 712 (1987)]. The results are shown in Table 3. As seen from Table 3, among 10 hygromycin B resistant transformants, 6 strains secreted Human lysozymm in the medium. Among these 6 strains, *Acremonium chrysogenum*/pNLH2 [IFO 32442, FERM BP-3848, deposited at Fermentation Research Institute (FRI) Japan under Budapest Treaty as of May 11, 1992] secretes the maximum amount of Human lysozyme in the medium.

TABLE 3

| Number of transformants | | Amount of human lysozyme (mg/liter) | |
|---|---|---|---|
| Hygromycin B resistant strain | Human lysozyme secretion strain | Average | Maximum |
| 10 | 6 | 36.2 | 46.3 |

5) Isolation and purification of human lysozyme

The culture solution obtained in the above 4) was centrifuged to obtain a supernatant (1.4 liters) and the supernatant was dialyzed against 50 mM sodium phosphate buffer (pH 6.7). The dialyzate was applied onto a column of CM Toyopearl 650M (manufactured by Tosoh, Japan) equilibrated with the same buffer. The column was washed with the same buffer and the absorbates were eluted with a linear gradient of NaCl (0 to 0.7M) to obtain an active fraction. The fraction was applied onto a column of TSK gel ODS-120T (manufactured by Tosoh, Japan) equilibrated with water containing 0.1% TFA. The column was washed with the same buffer and the human lysozyme was eluted with a linear gradient of acetonitrile (0 to 80%). The eluent was lyophilized. The enzyme was subjected to SDS polyacrylamide gel electrophoresis to give a single band. This migration location was confirmed to be the same as that of a commercially available human lysozyme standard.

---

What is claimed is:

1. An isolated and purified DNA fragment comprising a nucleotide sequence coding for a promoter region comprising the nucleotide sequence of nucleotides 1 to 541 of SEQ ID No: 1.

2. An isolated and purified DNA fragment comprising a nucleotide sequence coding for a secretion peptide comprising the amino acid sequence of amino acids 1 to 14 of SEQ ID No: 2.

3. An isolated and purified DNA fragment comprising a nucleotide sequence coding for a promoter region comprising the nucleotide sequence of nucleotides 1 to 541 of SEQ ID No: 1 and a nucleotide sequence coding for a secretion peptide comprising the amino acid sequence of amino acids 1 to 14 of SEQ ID No: 2.

4. A plasmid comprising the DNA fragment of claim 1.

5. A plasmid comprising the DNA fragment of claim 2.

6. A plasmid comprising the DNA fragment of claim 3.

7. A microorganism transformed with the plasmid of claim 4.

8. A microorganism transformed with the plasmid of claim 5.

9. A microorganism transformed with the plasmid of claim 6.

* * * * *

UNITED STATES PATENT AND TRADEMARK OFFICE
CERTIFICATE OF CORRECTION

PATENT NO. : 5,543,322
DATED : August 6, 1996
INVENTOR(S) : Kazuaki KITANO et al.

It is certified that error appears in the above-indentified patent and that said Letters Patent is hereby corrected as shown below:

On the cover page, in item [30] *Foreign Application Priority Data*, change "May 21, 1991" to --May 22, 1991--.

Signed and Sealed this

Twenty-sixth Day of November 1996

Attest:

BRUCE LEHMAN

*Attesting Officer*     *Commissioner of Patents and Trademarks*

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 2845 base pairs
        ( B ) TYPE: nucleic acid
        ( C ) STRANDEDNESS: double
        ( D ) TOPOLOGY: linear ( i i ) MOLECULE TYPE: Genomic DNA ( i i i ) HYPOTHETICAL:

( i v ) ANTI-SENSE:

( v ) FRAGMENT TYPE:

( v i ) ORIGINAL SOURCE:
        ( A ) ORGANISM: Fusarium sp.
        ( B ) STRAIN: S-19-5 (IFO 8884)
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE:
        ( A ) LIBRARY:
        ( B ) CLONE:

( v i i i ) POSITION IN GENOME:
        ( A ) CHROMOSOME/SEGMENT:
        ( B ) MAP POSITION:
        ( C ) UNITS:

( i x ) FEATURE:
        ( A ) NAME/KEY:
        ( B ) LOCATION:
        ( C ) IDENTIFICATION METHOD:
        ( D ) OTHER INFORMATION:

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( H ) DOCUMENT NUMBER:
        ( I ) FILING DATE:
        ( J ) PUBLICATION DATE:
        ( K ) RELEVANT RESIDUES IN SEQ ID NO:

( x i ) SEQUENCE DESCRIPTION: SEQ ID NO:1:

```
GGATCCGAAA  GATGAGACCG  CTTTCATGCT  CACACTTGCT  AGTCCACCGA  CGGCATATGG      60

CCAAGATGCC  ACTCCACGCC  ATTATTCCGG  GAGTTTCGCT  TCTCGACTCG  CAGAACCCAC     120

TCCTCCAATA  TCATCAAACT  AGCATTGATC  GAGAAGCTCC  AAAGGCACAG  TGTCGCATTG     180

TACAGAGGGA  TTGGCAATTC  GCCGCTGTCC  CATGGCCTCA  AGACCTTCCA  GATTCTCTCA     240

GCTCAGCTCA  TCTGACAAAT  TAAGCTCAGC  AGCATCGCCT  CTTCTTTATT  GATCCTTTGT     300

TCTAGCCCAA  GTCCCCCGTC  GCATCCACGC  TGGAAATGGC  AGGTAGCAAG  AACTTGTTCG     360
```

```
ACATTGAAGA GTGGGATGCC GACTCGCCGA AGATTGAGTA GCTCGTCCAG CAAAGACGAC    420
GGTGAAAGAT AAATAGCAGC TGCGGCCCCG TGAAATGAAT TGTTCCTCAT CAAGCTCACA    480
GTTTCATTAG CAAACAGTCT TTCCAAAAAC TCACTTCTCA ACCTTCATAC TCCCTGACAA    540
GATGCGTCTG TCCATCATCG CAGTCCTTCC CCTGGCCCTC GCGGCCCCGG TCCTGGAACC    600
CGCTCCTCTC CTCGAGGCTC GTGGTTCGCA GCCCATTGCT GGCAAGTACA TTGTCAAGCT    660
CAAGGACACC GCCAAGATTG GCATCATGGA GGCCACGGCC AAGGTGGCCA ACCCTGAACG    720
TGTCTACCAG AACGTCATCA AGGGATTCTC CGCTTCCCTC AGCAAGGAAG AGGTTGAGCG    780
TCTCCGCCAC GACCCTGATG TAAGTGCAAC ACGTTGTACT AAAGTAAGAC GACGTTGACC    840
ATTTTTGGGA AATAGGTCGA GTCTATTGAG CAGGATGCCA TCATCAGCAT CAACGCTATT    900
ACCCAGCAGC AGGGCGCAAC TTGGGGACTT ACCCGCATCT CCCACCGCCA GCGTGGCAGC    960
ACCGCGTATG CCTACGACAC GACCGCCGGA CAGGGTGCCT GCGCCTATGT CATTGACACC   1020
GGTGTTGAGG ACACTCACCC CGTAAGCTCT TGCATGTTTA TGGTCAAAAT GTATGCCAGT   1080
TGCTAATGGA AGTGAAATGT AGGAGTTTGA AGGACGTGCC AAGCAGATCA AGACCTTTGC   1140
CAGCACCGCC CGTGACGGCA ACGGCCACGG CACCCACTGC TCCGGCACCA TTGGCTCCAA   1200
AACATATGGT GTCGCCAAGA AGGTCTCCAT CTTCGGTGTC AAGGTCCTGG ACGACAACGG   1260
CTCGGGCTCG CTCAGCAATG TCATTGCCGG CATGGACTTT GTCGCCTCTG ACTACCGCTC   1320
TCGCAACTGC CCTCGTGGTG TCGTTGCCAG CATGTCTCTT GGTGGTGGTT ACTCGGCCAC   1380
CGTGAACCAG GCTGCCGCCC GTCTGCAGTC CTCTGGCGTC TTTGTCGCTG TCGCCGCTGG   1440
CAACGACAAC CGTGATGCTG CCAACACTTC GCCCGCCTCG GAGCCCTCGG TTTGCACCGT   1500
CGGCGCTACT GACTCGTCCG ATCGTCGCTC GTCTTTCTCC AACTATGGTC GTGCCCTTGA   1560
TATTTTCGCT CCCGGCACTG ACATCACCTC CACCTGGATT GGCGGCCGCA CGGTAAGTTC   1620
CTGTCGCGTT TTGTGGTCTT GTGTTCCAGA CAACTAACCT GTTGACTCTA GAACACCATC   1680
TCTGGAACCT CCATGGCTAC TCCCCACATT GCTGGTCTCG GTGCCTACCT TCTGGCTCTC   1740
GAGGGTGGCA GTGCCAGCAC TATCTGTGCT CGTATCCAGA CTCTCTCCAC CAAGAATGCC   1800
ATCTCGGGCG TTCCCTCGGG TACCGTCAAC TACCTGGCCT TCAACAACGC CACGTGAGTG   1860
AGTCAGTAAT CACTCATCTG GAGGCATGAA GGCTGGATGA ACGGAGGGCG CATGTCCTAT   1920
ACAACTGCCG GTCAGCAATG TTAATGCAGA CCTCATCGCT GCCTAGGGAT CGATTGCCGA   1980
GGTATTGGTT TCATTTTGCT TTTTATGTGA CTTTGAGGTG TCTCCTCCGC CAAGTACATA   2040
GTCAATAAGA GTGTTTTGCA CTATACGAAC AGCCACCGTG ACCCGTAAAG CATCGCAGCC   2100
ATGGCGTTCT CTTGTGACGC ATCTGTATGT ATGCTTCTGG AGATTTACAG AGAAAATTAA   2160
CTCTATTCGG ACAATTTACG AAGGATGCAG TACCCTGCAC GAGCCGACAG CTCGGCACAT   2220
CGAGAATCTT CAGCTGGGAG AGCTGAAGCC TCGATACCAA AGTCACATGC TATACTTTGG   2280
TGGCTTGATT ATATCAGAAT GCGACATCG GTACAGATTG ATCATTTAA GGCAACCATC    2340
AGTTTATTTC CAGCCACGTC AACATGGCGT TATGGCTGGT TTTGGGCGTG AATCGGTAAC   2400
TGCACCCGAC GAAGCAGGTG GAGCCGACCG TGGGATGGAA CCGGCTTGTC AGTTTCTCGC   2460
CGTGGGCACG GAAAACACAG CCATCCGGGT ACGCGGACAG GTCAGAGATA ATTCAGGCAG   2520
CCATTGCACG AGAATCTGAC TAGTCCGTGC TGGATTTGTG GTTCAAAACA GAGCCTGACA   2580
GGCAGCCGAG ACTAGTTGTT GACGTGCAGG TCGCAAGGGG CACATGGTTA TGGTGTGCTG   2640
TGAATGCCGA ATGAGTTGAA GGGGCTCAGT AGTTTGAGTT TGAACATGGT GTCCGTTGGC   2700
CGATGTGGAG GAGAGCAACA AGTCCACAGT TGCAGCTAAC AAGCCAGCCA GCCGCAAGTG   2760
```

```
CAAAGAAATG GGTTTAGGAC AATCTCGTAC AATGGGGATT CGAGTTTCGT TGCTCCTCGT        2820

TTCTTTATTT AGAGGTCCTG GATCC                                             2845
```

( 2 ) INFORMATION FOR SEQ ID NO:2:

( i ) SEQUENCE CHARACTERISTICS:
        ( A ) LENGTH: 1140 base pairs
        ( B ) TYPE: nucleic acid
        ( C ) STRANDEDNESS: double
        ( D ) TOPOLOGY: linear ( i i ) MOLECULE TYPE: Genomic DNA ( i i i ) HYPOTHETICAL:

( i v ) ANTI-SENSE:

( v ) FRAGMENT TYPE:

( v i ) ORIGINAL SOURCE:
        ( A ) ORGANISM: Fusarium sp.
        ( B ) STRAIN: S-19-5 (IFO 8884)
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE:
        ( A ) LIBRARY:
        ( B ) CLONE:

( v i i i ) POSITION IN GENOME:
        ( A ) CHROMOSOME/SEGMENT:
        ( B ) MAP POSITION:
        ( C ) UNITS:

( i x ) FEATURE:
        ( A ) NAME/KEY:
        ( B ) LOCATION:
        ( C ) IDENTIFICATION METHOD:
        ( D ) OTHER INFORMATION:

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( H ) DOCUMENT NUMBER:
        ( I ) FILING DATE:
        ( J ) PUBLICATION DATE:
        ( K ) RELEVANT RESIDUES IN SEQ ID NO:

( x i ) SEQUENCE DESCRIPTION: SEQ ID NO:2:

```
ATG  CGT  CTG  TCC  ATC  ATC  GCA  GTC  CTT  CCC  CTG  GCC  CTC  GCG  GCC  CCG        48
Met  Arg  Leu  Ser  Ile  Ile  Ala  Val  Leu  Pro  Leu  Ala  Leu  Ala  Ala  Pro
 1              5                        10                       15

GTC  CTG  GAA  CCC  GCT  CCT  CTC  CTC  GAG  GCT  CGT  GGT  TCG  CAG  CCC  ATT        96
Val  Leu  Glu  Pro  Ala  Pro  Leu  Leu  Glu  Ala  Arg  Gly  Ser  Gln  Pro  Ile
              20                        25                       30

GCT  GGC  AAG  TAC  ATT  GTC  AAG  CTC  AAG  GAC  ACC  GCC  AAG  ATT  GGC  ATC       144
Ala  Gly  Lys  Tyr  Ile  Val  Lys  Leu  Lys  Asp  Thr  Ala  Lys  Ile  Gly  Ile
         35                        40                       45

ATG  GAG  GCC  ACG  GCC  AAG  GTG  GCC  AAC  CCT  GAA  CGT  GTC  TAC  CAG  AAC       192
Met  Glu  Ala  Thr  Ala  Lys  Val  Ala  Asn  Pro  Glu  Arg  Val  Tyr  Gln  Asn
 50                       55                       60

GTC  ATC  AAG  GGA  TTC  TCC  GCT  TCC  CTC  AGC  AAG  GAA  GAG  GTT  GAG  CGT       240
Val  Ile  Lys  Gly  Phe  Ser  Ala  Ser  Leu  Ser  Lys  Glu  Glu  Val  Glu  Arg
```

|  |  |  |  |  |  |  |  |  |  |  |  |  |  |  |  |  |
|---|---|---|---|---|---|---|---|---|---|---|---|---|---|---|---|---|
| 65 |  |  |  |  | 70 |  |  |  |  | 75 |  |  |  |  | 80 |  |
| CTC | CGC | CAC | GAC | CCT | GAT | GTC | GAG | TCT | ATT | GAG | CAG | GAT | GCC | ATC | ATC | 288 |
| Leu | Arg | His | Asp | Pro | Asp | Val | Glu | Ser | Ile | Glu | Gln | Asp | Ala | Ile | Ile |  |
|  |  |  |  | 85 |  |  |  |  | 90 |  |  |  |  | 95 |  |  |
| AGC | ATC | AAC | GCT | ATT | ACC | CAG | CAG | CAG | GGC | GCA | ACT | TGG | GGA | CTT | ACC | 336 |
| Ser | Ile | Asn | Ala | Ile | Thr | Gln | Gln | Gln | Gly | Ala | Thr | Trp | Gly | Leu | Thr |  |
|  |  |  | 100 |  |  |  |  | 105 |  |  |  |  | 110 |  |  |  |
| CGC | ATC | TCC | CAC | CGC | CAG | CGT | GGC | AGC | ACC | GCG | TAT | GCC | TAC | GAC | ACG | 384 |
| Arg | Ile | Ser | His | Arg | Gln | Arg | Gly | Ser | Thr | Ala | Tyr | Ala | Tyr | Asp | Thr |  |
|  |  | 115 |  |  |  |  | 120 |  |  |  |  | 125 |  |  |  |  |
| ACC | GCC | GGA | CAG | GGT | GCC | TGC | GCC | TAT | GTC | ATT | GAC | ACC | GGT | GTT | GAG | 432 |
| Thr | Ala | Gly | Gln | Gly | Ala | Cys | Ala | Tyr | Val | Ile | Asp | Thr | Gly | Val | Glu |  |
| 130 |  |  |  |  | 135 |  |  |  |  | 140 |  |  |  |  |  |  |
| GAC | ACT | CAC | CCC | GAG | TTT | GAA | GGA | CGT | GCC | AAG | CAG | ATC | AAG | ACC | TTT | 480 |
| Asp | Thr | His | Pro | Glu | Phe | Glu | Gly | Arg | Ala | Lys | Gln | Ile | Lys | Thr | Phe |  |
| 145 |  |  |  |  | 150 |  |  |  |  | 155 |  |  |  |  | 160 |  |
| GCC | AGC | ACC | GCC | CGT | GAC | GGC | AAC | GGC | CAC | GGC | ACC | CAC | TGC | TCC | GGC | 528 |
| Ala | Ser | Thr | Ala | Arg | Asp | Gly | Asn | Gly | His | Gly | Thr | His | Cys | Ser | Gly |  |
|  |  |  |  | 165 |  |  |  |  | 170 |  |  |  |  | 175 |  |  |
| ACC | ATT | GGC | TCC | AAA | ACA | TAT | GGT | GTC | GCC | AAG | AAG | GTC | TCC | ATC | TTC | 576 |
| Thr | Ile | Gly | Ser | Lys | Thr | Tyr | Gly | Val | Ala | Lys | Lys | Val | Ser | Ile | Phe |  |
|  |  |  | 180 |  |  |  |  | 185 |  |  |  |  | 190 |  |  |  |
| GGT | GTC | AAG | GTC | CTG | GAC | GAC | AAC | GGC | TCG | GGC | TCG | CTC | AGC | AAT | GTC | 624 |
| Gly | Val | Lys | Val | Leu | Asp | Asp | Asn | Gly | Ser | Gly | Ser | Leu | Ser | Asn | Val |  |
|  |  | 195 |  |  |  |  | 200 |  |  |  |  | 205 |  |  |  |  |
| ATT | GCC | GGC | ATG | GAC | TTT | GTC | GCC | TCT | GAC | TAC | CGC | TCT | CGC | AAC | TGC | 672 |
| Ile | Ala | Gly | Met | Asp | Phe | Val | Ala | Ser | Asp | Tyr | Arg | Ser | Arg | Asn | Cys |  |
| 210 |  |  |  |  | 215 |  |  |  |  | 220 |  |  |  |  |  |  |
| CCT | CGT | GGT | GTC | GTT | GCC | AGC | ATG | TCT | CTT | GGT | GGT | GGT | TAC | TCG | GCC | 720 |
| Pro | Arg | Gly | Val | Val | Ala | Ser | Met | Ser | Leu | Gly | Gly | Gly | Tyr | Ser | Ala |  |
| 225 |  |  |  |  | 230 |  |  |  |  | 235 |  |  |  |  | 240 |  |
| ACC | GTG | AAC | CAG | GCT | GCC | GCC | CGT | CTG | CAG | TCC | TCT | GGC | GTC | TTT | GTC | 768 |
| Thr | Val | Asn | Gln | Ala | Ala | Ala | Arg | Leu | Gln | Ser | Ser | Gly | Val | Phe | Val |  |
|  |  |  |  | 245 |  |  |  |  | 250 |  |  |  |  | 255 |  |  |
| GCT | GTC | GCC | GCT | GGC | AAC | GAC | AAC | CGT | GAT | GCT | GCC | AAC | ACT | TCG | CCC | 816 |
| Ala | Val | Ala | Ala | Gly | Asn | Asp | Asn | Arg | Asp | Ala | Ala | Asn | Thr | Ser | Pro |  |
|  |  |  | 260 |  |  |  |  | 265 |  |  |  |  | 270 |  |  |  |
| GCC | TCG | GAG | CCC | TCG | GTT | TGC | ACC | GTC | GGC | GCT | ACT | GAC | TCG | TCC | GAT | 864 |
| Ala | Ser | Glu | Pro | Ser | Val | Cys | Thr | Val | Gly | Ala | Thr | Asp | Ser | Ser | Asp |  |
|  |  | 275 |  |  |  |  | 280 |  |  |  |  | 285 |  |  |  |  |
| CGT | CGC | TCG | TCT | TTC | TCC | AAC | TAT | GGT | CGT | GCC | CTT | GAT | ATT | TTC | GCT | 912 |
| Arg | Arg | Ser | Ser | Phe | Ser | Asn | Tyr | Gly | Arg | Ala | Leu | Asp | Ile | Phe | Ala |  |
| 290 |  |  |  |  | 295 |  |  |  |  | 300 |  |  |  |  |  |  |
| CCC | GGC | ACT | GAC | ATC | ACC | TCC | ACC | TGG | ATT | GGC | GGC | CGC | ACG | AAC | ACC | 960 |
| Pro | Gly | Thr | Asp | Ile | Thr | Ser | Thr | Trp | Ile | Gly | Gly | Arg | Thr | Asn | Thr |  |
| 305 |  |  |  |  | 310 |  |  |  |  | 315 |  |  |  |  | 320 |  |
| ATC | TCT | GGA | ACC | TCC | ATG | GCT | ACT | CCC | CAC | ATT | GCT | GGT | CTC | GGT | GCC | 1008 |
| Ile | Ser | Gly | Thr | Ser | Met | Ala | Thr | Pro | His | Ile | Ala | Gly | Leu | Gly | Ala |  |
|  |  |  |  | 325 |  |  |  |  | 330 |  |  |  |  | 335 |  |  |
| TAC | CTT | CTG | GCT | CTC | GAG | GGT | GGC | AGT | GCC | AGC | ACT | ATC | TGT | GCT | CGT | 1056 |
| Tyr | Leu | Leu | Ala | Leu | Glu | Gly | Gly | Ser | Ala | Ser | Thr | Ile | Cys | Ala | Arg |  |
|  |  |  | 340 |  |  |  |  | 345 |  |  |  |  | 350 |  |  |  |
| ATC | CAG | ACT | CTC | TCC | ACC | AAG | AAT | GCC | ATC | TCG | GGC | GTT | CCC | TCG | GGT | 1104 |
| Ile | Gln | Thr | Leu | Ser | Thr | Lys | Asn | Ala | Ile | Ser | Gly | Val | Pro | Ser | Gly |  |
|  |  | 355 |  |  |  |  | 360 |  |  |  |  | 365 |  |  |  |  |
| ACC | GTC | AAC | TAC | CTG | GCC | TTC | AAC | AAC | GCC | ACG | TGA |  |  |  |  | 1140 |
| Thr | Val | Asn | Tyr | Leu | Ala | Phe | Asn | Asn | Ala | Thr |  |  |  |  |  |  |
| 370 |  |  |  |  | 375 |  |  |  |  |  |  |  |  |  |  |  |

( 2 ) INFORMATION FOR SEQ ID NO:3:

```
    ( i ) SEQUENCE CHARACTERISTICS:
            ( A ) LENGTH: 20 amino acids
            ( B ) TYPE: amino acid
            ( C ) STRANDEDNESS: single
            ( D ) TOPOLOGY: linear ( i i ) MOLECULE TYPE:

( i i i ) HYPOTHETICAL:

( i v ) ANTI-SENSE:

( v ) FRAGMENT TYPE:

( v i ) ORIGINAL SOURCE:
            ( A ) ORGANISM:
            ( B ) STRAIN:
            ( C ) INDIVIDUAL ISOLATE:
            ( D ) DEVELOPMENTAL STAGE:
            ( E ) HAPLOTYPE:
            ( F ) TISSUE TYPE:
            ( G ) CELL TYPE:
            ( H ) CELL LINE:
            ( I ) ORGANELLE:

( v i i ) IMMEDIATE SOURCE:
            ( A ) LIBRARY:
            ( B ) CLONE:

( v i i i ) POSITION IN GENOME:
            ( A ) CHROMOSOME/SEGMENT:
            ( B ) MAP POSITION:
            ( C ) UNITS:

( i x ) FEATURE:
            ( A ) NAME/KEY:
            ( B ) LOCATION:
            ( C ) IDENTIFICATION METHOD:
            ( D ) OTHER INFORMATION:

( x ) PUBLICATION INFORMATION:
            ( A ) AUTHORS:
            ( B ) TITLE:
            ( C ) JOURNAL:
            ( D ) VOLUME:
            ( E ) ISSUE:
            ( F ) PAGES:
            ( G ) DATE:
            ( H ) DOCUMENT NUMBER:
            ( I ) FILING DATE:
            ( J ) PUBLICATION DATE:
            ( K ) RELEVANT RESIDUES IN SEQ ID NO:

( x i ) SEQUENCE DESCRIPTION: SEQ ID NO:3:

Ala  Ile  Thr  Gln  Gln  Gln  Gly  Ala  Thr  Trp  Gly  Leu  Thr  Arg  Ile
 1                  5                       10                         15

Ser  His  Arg  Gln  Arg
                    20

( 2 ) INFORMATION FOR SEQ ID NO:4:

( i ) SEQUENCE CHARACTERISTICS:
            ( A ) LENGTH: 10 amino acids
            ( B ) TYPE: amino acid
            ( C ) STRANDEDNESS: single
            ( D ) TOPOLOGY: linear ( i i ) MOLECULE TYPE:

( i i i ) HYPOTHETICAL:

( i v ) ANTI-SENSE:

( v ) FRAGMENT TYPE:

( v i ) ORIGINAL SOURCE:
```

```
            (A) ORGANISM:
            (B) STRAIN:
            (C) INDIVIDUAL ISOLATE:
            (D) DEVELOPMENTAL STAGE:
            (E) HAPLOTYPE:
            (F) TISSUE TYPE:
            (G) CELL TYPE:
            (H) CELL LINE:
            (I) ORGANELLE:

(vii) IMMEDIATE SOURCE:
            (A) LIBRARY:
            (B) CLONE:

(viii) POSITION IN GENOME:
            (A) CHROMOSOME/SEGMENT:
            (B) MAP POSITION:
            (C) UNITS:

(ix) FEATURE:
            (A) NAME/KEY:
            (B) LOCATION:
            (C) IDENTIFICATION METHOD:
            (D) OTHER INFORMATION:

(x) PUBLICATION INFORMATION:
            (A) AUTHORS:
            (B) TITLE:
            (C) JOURNAL:
            (D) VOLUME:
            (E) ISSUE:
            (F) PAGES:
            (G) DATE:
            (H) DOCUMENT NUMBER:
            (I) FILING DATE:
            (J) PUBLICATION DATE:
            (K) RELEVANT RESIDUES IN SEQ ID NO:

(xi) SEQUENCE DESCRIPTION: SEQ ID NO:4:

Asp  Ile  Phe  Ala  Pro  Gly  Thr  Asp  Ile  Thr
 1                  5                        10
```